US010596122B2

(12) United States Patent
Powell et al.

(10) Patent No.: US 10,596,122 B2
(45) Date of Patent: Mar. 24, 2020

(54) AMORPHOUS MAGNESIUM-SUBSTITUTED CALCIUM PHOSPHATE COMPOSITIONS AND THEIR USES

(71) Applicant: Medical Research Council, Swindon Wiltshire (GB)

(72) Inventors: Jonathan Joseph Powell, Cambridge (GB); Nuno Jorge Rodriguez Faria, Bedfordshire (GB); Laetitia Pele, Cambridge (GB); Rachel Hewitt, Cambridge (GB); Emma Thomas-McKay, Oxfordshire (GB)

(73) Assignee: Medical Research Council, Swindon Wiltshire (GB)

( * ) Notice: Subject to any disclaimer, the term of this patent is extended or adjusted under 35 U.S.C. 154(b) by 0 days.

(21) Appl. No.: 15/033,750

(22) PCT Filed: Nov. 5, 2014

(86) PCT No.: PCT/GB2014/053291

§ 371 (c)(1),
(2) Date: May 2, 2016

(87) PCT Pub. No.: WO2015/067939

PCT Pub. Date: May 14, 2015

(65) Prior Publication Data

US 2016/0235683 A1 Aug. 18, 2016

(30) Foreign Application Priority Data

Nov. 5, 2013 (GB) .................................. 1319548.2

(51) Int. Cl.

| | |
|---|---|
| ***A61K 49/00*** | (2006.01) |
| ***A61K 9/50*** | (2006.01) |
| ***A61K 9/51*** | (2006.01) |
| ***C01B 25/32*** | (2006.01) |
| ***A61K 47/02*** | (2006.01) |
| ***A61K 9/16*** | (2006.01) |
| *A61K 39/00* | (2006.01) |

(52) U.S. Cl.

CPC ............ *A61K 9/501* (2013.01); *A61K 9/1611* (2013.01); *A61K 9/5115* (2013.01); *A61K 47/02* (2013.01); *A61K 49/0002* (2013.01); *C01B 25/32* (2013.01); *A61K 39/00* (2013.01)

(58) Field of Classification Search

None

See application file for complete search history.

(56) References Cited

U.S. PATENT DOCUMENTS

| | | | | |
|---|---|---|---|---|
| 5,443,832 | A | 8/1995 | Amerongen et al. | |
| 6,541,037 | B1 | 4/2003 | Lee et al. | |
| 2012/0128767 | A1* | 5/2012 | Lee ..................... | A61K 9/5115 424/452 |

FOREIGN PATENT DOCUMENTS

| | | | |
|---|---|---|---|
| EP | 1 872 798 | A1 | 1/2008 |
| WO | 2008/072155 | A1 | 6/2008 |
| WO | 2015067939 | A1 | 5/2015 |

OTHER PUBLICATIONS

Lee et al (Novel in-situ synthesis and characterization of nanostructured magnesium substituted β-tricalcium phosphate (β-TCMP). Materials Science and Engineering C 29 (2009) 69-77).*
Hewitt et al (Immuno-inhibitory PD-L1 can be induced by a Peptidoglycan/NOD2 mediated pathway in primary monocytic cells and is deficient in Crohn's patients with homozygous NOD2 mutations. Clinical Immunology (2012) 143, 162-169).*
Sandborn et al (Biologics in inflammatory bowel disease: how much progress have we made? Gut. Sep. 2004; 53(9): 1366-1373).*
Bhakta, Gajadhar et al., "Magnesium phosphate nanoparticles can be efficiently used in vitro and in vivo as non-viral vectors for targeted gene delivery", Journal of Biomedical Nanotechnology, 5(1): 106-114 (2009.
Chowdhury, E.H. et al., "High-efficiency gene delivery for expression in mammalian cells by nanoprecipitates of Ca—Mg phosphate", Gene, 341: 77-82 (2004).
Chowdhury, E.H. et al., "Fibronectin-coated nano-precipitates of calcium-magneisum phosphate phosphate for integrin-targeted gene delivery", Journal of Controlled Release, 116(2): e68-e69 (2006).
Dasgupta, Sudip et al., "Zn and Mg Doped Hydroxyapatite Nanoparticles for Controlled Release of Protein", Langmuir, 26(7): 4958-4964 (2010).
Kim, Tae-Wan et al., "In situ synthesis of magnesium-substituted biphasic calcium phosphate and in vitro biodegradation", Materials Research Bulletin, 47: 2506-2512 (2012).
Giocondi, Jennifer L. et al., "Molecular mechanisms of crystallization impacting calcium phosphate cements", Phil. Trans. R. Soc. A, 368: 1937-1962 (2010).
Lee, Donghyun et al., "Novel in-situ synthesis and characerization of nanostructured magnesium substituted B-tricalcium phosphate (B-TCMP)", Materials Science and Engineering, C29: 69-77 (2009).
Joyappa, Dechamma et al., "Calcium phosphate nanoparticle prepared with foot and mouth disease virus P1-3CD gene construct protects mice and guinea pigs against the challenge virus", Veterinary Microbiology, 139: 58-66 (2009).
Paul, Willi et al., "Synthesis and characterization of alginate coated zinc calcium phosphate nanoparticles for intestinal delivery of insulin", Process Biochemistry, 47: 882-886 (2012).
International Search Report/Written Opinion, dated Jan. 30, 2015, issued in corresponding International Application No. PCT/GB2014/053291, filed Nov. 5, 2014.

(Continued)

*Primary Examiner* — Jake M Vu

(74) *Attorney, Agent, or Firm* — Kathleen D. Rigaut; Howson & Howson LLP

(57) ABSTRACT

Amorphous magnesium-substituted calcium, phosphate compositions and their medical uses are described, in particular for use in delivering cargo materials, such as cargo molecules or cargo nanoparticles contained in pores of the amorphous magnesium-substituted calcium phosphate to cells of the immune system, for example as therapeutic approaches for the treatment of inflammatory bowel diseases, and in particular Crohn's disease, autoimmune diseases, allergy and for therapeutic vaccination.

12 Claims, 7 Drawing Sheets

Specification includes a Sequence Listing.

(56) References Cited

OTHER PUBLICATIONS

UK Search Report, dated May 13, 2014, issued in corresponding GB Application No. 1319548.2.
Adolph, Timon E. et al., "Paneth cells as a site of origin for intestinal inflammation", Nature, 503: 272-276 (2013).
Bamias, Giorgos et al., "Intestinal-Specific TNFalpha Overexpression Induces Crohn's Like Ileitis in Mice", PLoS One, 8(8): e72594 (2013).
Boskey, Adele Ludin et al., "Conversion of Amorphous Calcium Phosphate to Microcrystalline Hydroxyapatite, a pH-Dependent, Solution-Mediated, Solid-Solid Conversion", The Journal of Physical Chemistry, 77(19): 2313-2317 (1973).
Boskey, A.L. et al., "Magnesium Stabilization of Amorphous Calcium Phosphate: A Kinetic Study", Mat. Res. Bull., 9: 907-916 (1974).
Den Hartog, Gerco et al., "The Mucosal Factors Retinoic Acid and TGF-B1 Induce Phenotypically and Functionally Distinct Dendritic Cell Types", Int. Arch. Allergy Immunol., 225-236 (2013).
Dong, Haidong et al., "Tumor-associated B7-H1 promotes T-cell apoptosis: A potential mechanism of immune evasion", Nature Medicine, 8(8): 793-800 (2002).
Gong, Ai-Yu et al., "MicroRNA-513 Regulates B7-H1 Translation and Is Involved in IFN-gamma-Induced B7-H1 Expression in Cholangiocytes", J. Immunol., 182: 1325-1333 (2009).
Iliev, I.D. et al., "Human intestinal epithelial cells promote the differentiation of tolerogenic dendritic cells", Gut, 58: 1481-1489 (2009).
Iliev, I.D. et al., "Intestinal epithelial cells promote colitis-protective regulatory T-cell differentiation through dendritic cell conditioning", Nature, 2(4): 340-350 (2009).
Desouky, Mahmoud et al., "Aluminum-dependent regulation of intracellular silicon in the aquatic invertebrate Lymnaea stagnalis", 99(6): 3394-3399 (2002).
Kan-O, Keiko et al., "P13K-delta mediates double-stranded RNA-induced upregulation of B7-H1 in BEAS-2B airway epithelial cells", Biochemical and Biophysical Research Communications, 435: 195-201 (2013).
Lee, Seung-Jin et al., "INterferon regulatory factor-1 is prerequisite to the constitutive expression and IFN-gamma-induced upregulation of B7-H1 (CD274)", FEBS Letters, 580: 755-762 (2006).
Li, Yanbao et al., "In vitro synthesis and characterization of amorphous calcium phosphates with various Ca/P atomic rattios", J. Mater Sci: Mater Med., 18: 2303-2308 (2007).
Maheshwari, Akhil et al., "TGF-B2 Suppresses Macrophage Cytokine Production and Mucosal Inflammatory Responses in the Developing Intestine", Gastroenterology, 140: 242-253 (2011).
Mann, Elizabeth R. et al., "Human Gut-Specific Homeostatic Dendritic Cells are Generated from Blood Precursors by the Gut Microenvironment", Inflamm. Bowel Dis., 18(7): 1275-1286 (2012).
Rimoldi, Monica et al., "Intestinal immune homeostasis is regulated by the crosstalk between epithelial cells and dendritic cells", Nature Immunology, 6(5): 507-514 (2005).
Sakai, Shunsuke et al., "PD-1-PD-L1 pathway impairs Th1 immune response in the late stage of infection with *Mycobacterium bovis bacillus* Calmette-Guerin", International Immunology, 22(12): 915-925 (2010).
Seyerl, Maria et al., "Human rhinoviruses induce Il-35-producing Treg via induction of B7-I-11 (CD274) and sialoadhesin (CD169) on DC", Eur. J. Immunol., 40: 321-329 (2010).
Steinbrink, Kerstin et al., "Induction of Tolerance by IL-10-Treated Dendritic Cells", The Journal of Immunology, 159: 4772-4780 (1997).
Trabattoni, Dania et al., "B7-H1 is up-regulated in HIV infection and is a novel surrogate marker of disease progression", Blood, 101: 2514-2520 (2003).
Zeuthen, Louise et al., "Toll-like receptor 2 and nucleotide-binding oligomerization domain-2 play divergent roles in the recognition of gut-derived lactobacilli and bifidobacgteria in dendritic cells", Immunology, 124: 489-502 (2008).
Zhao, Jie et al., "Amorphous calcikum phosphate and its application in dentistry", Chemistry Central Journal, 5: 40 (2011).
Epple, M. et al., "Application of calcium phosphate nanoparticles in biomedicine", J. Mater. Chem., 20: 18-23 (2010).
Hewitt, Rachel E. et al., "Immuno-inhibitory PD-L1 can be induced by a Peptidoglycan/NOD2 mediated pathway in primary monocytic cells and is deficient in Crohn's patients with homozygous NOD2 mutations", Clinical Immunology, 143: 162-169 (2012).
Rieux, Anne des et al., "Nanoparticles as potential oral delivery systems of proteins and vaccines: A mechanistic approach", Journal of Controlled Release, 116: 1-27 (2006).
English translation of Japanese Official Action, dated Jun. 27, 2018, issued in corresponding Japanese Application No. 2016-551077.

* cited by examiner

AMORPHOUS MAGNESIUM-SUBSTITUTED CALCIUM PHOSPHATE COMPOSITIONS AND THEIR USES

CROSS-REFERENCE TO RELATED APPLICATIONS

This application is a § 371 of International Application No. PCT/GB2014/053291, filed Nov. 5, 2014, which claims priority from Great Britain Patent Application No. 1319548.2, filed Nov. 5, 2013. The entire disclosure of each of the aforesaid applications is incorporated by reference in the present application.

INCORPORATION-BY-REFERENCE OF MATERIAL SUBMITTED IN ELECTRONIC FORM

Incorporated herein by reference in its entirety is the Sequence Listing submitted via EFS-Web as a text file named PowellSequenceListing.txt., created Feb. 5, 2020 and having a size of 2,877 bytes.

FIELD OF THE INVENTION

The present invention relates to amorphous magnesium-substituted calcium phosphate compositions and their medical uses, and more particularly to amorphous magnesium-substituted calcium phosphate compositions for use in delivering cargo materials, such as cargo molecules or cargo nanoparticles contained in pores of the amorphous magnesium-substituted calcium phosphate to cells of the immune system. In further aspects, the present, invention relates to novel therapeutic approaches for the treatment of inflammatory bowel diseases, and in particular Crohn's disease, autoimmune diseases, allergy and for therapeutic vaccination, and the amorphous magnesium-substituted calcium phosphate compositions for use in diagnosis.

BACKGROUND OF THE INVENTION

Calcium phosphate is the name given to a family of minerals containing calcium ions ($Ca^{2+}$), together with orthophosphates ($PO_4^{3-}$), metaphosphates or pyrophosphates ($P_2O_7^{4-}$) and hydrogen or hydroxide ions. One of the naturally occurring forms of calcium phosphate present in bones and tooth enamel is biological hydroxyapatite (HA) which has the approximate formula $Ca_5(PO_4)_3(OH)$, usually written $Ca_{10}(PO_4)_6(OH)_2$. In the biological field, synthetic crystalline hydroxyapatite is used in tissue engineering, primarily as a filler material for repairing bones and teeth. Nanoparticles of hydroxyapatite have also been proposed as carriers for drugs and have been employed in imaging techniques.

Hydroxyapatite can be prepared in a precipitation reaction of calcium and dibasic phosphate salts in neutral or basic solution and has as its final product crystalline hydroxyapatite. However, during precipitation, a structurally and chemically distinct precursor phase is formed which is amorphous to X-ray diffraction, known as amorphous calcium phosphate (ACP).

Chemical analysis of the precursor phase indicates this non crystalline phase is a hydratea calcium phosphate. As with other amorphous materials, several formulae have been proposed for ACP, such as $Ca_9(PO_4)_6$.

Hydroxyapatites have been used as carriers for biomolecules, in particular for DNA transfaction, drug delivery, and in orthopaedics and dentistry. By way of example, Chowdhury et al. have investigated delivery of DNA to mammalian cells in culture by precipitating DNA with calcium phosphate in the form of crystalline hydroxyapatite (see Gene, 341: 77-82, 2004; J. Controlled Release, 116(2): e68-e69, 2006; Analytical Biochemistry, 328: 96-97, 2004; US 2007/0077306). These experiments included using $Mg^{2+}$ as an agent to inhibit the growth of particles of precipitated hydroxyapatite and DNA to avoid a loss of transfection efficiency associated with an increase in particle size. However, while $Mg^{2+}$ was incorporated into the apatite particles precipitated with DNA, the particles remained, crystalline, Dasgupta et al. reported the use of Zn- and Mg-doped hydroxyapatite nanoparticles as controlled release carriers for bovine serum, albumin (Langmuir, 26(7): 4958-4964, 2010). However, as with the studies reported by Chowdhury et al., the doped, hydroxyapatite materials produced retained a clear degree of crystallinity in common with unmodified hydroxyapatite.

During synthesis, ACP rapidly converts (in the presence of water) to microcrystalline hydroxyapatite and the lifetime of the metastable ACP in aqueous solution has been reported to be a function of the presence of certain macromolecules and interfering ions, pH, viscosity, ionic strength and temperature. Boskey & Posner (1973, 1974) studied the kinetics of the conversion and found that substitution of Ca ions in ACP by Mg ions leads to greater stability of the amorphous state, lessening its tendency to convert through to more crystalline phases such as hydroxyapatite. They showed that at a ratio of at least 1:25 (Mg:Ca), an amorphous magnesium calcium phosphate phase is produced that, as a dry powder, remains stable over time.

While the synthesis of ACP has been reported, only very limited applications of this material have been proposed in the fields of dentistry and tissue engineering as a structural material for use in repairing bones and teeth and as a scaffold for tissue engineering. By way of example, Zhao et al. (Chemistry Central Journal, 5: 40-47, 2011) describe the use of amorphous calcium phosphate in dentistry as a composite for re-mineralising and repairing teeth. They report that in the presence of other ions and under in vivo conditions, ACP may persist for appreciable periods due to kinetic stabilization in the presence of $Mg^{2+}$, $F^-$, carbonate, pyrophosphate, diphosphonates, or polyphosphorylated metabolites or nucleotides, preventing the transformation of synthetic ACP to hydroxyapatite. Li & Weng (J. Mater. Sci.: Mater. Med., 18: 2303-2308, 2007) reported the synthesis of amorphous calcium phosphates (ACP) and were using poly(ethylene glycol) as stabilizing additive at low temperature. They found that ACP could be stabilized by poly(ethylene glycol) in the mother solution for more than 18 hours at 5° C. with 4 w.t. % poly(ethylene glycol) in ACP powders and suggested that ACP might be used as biodegradable scaffold for tissue engineering.

Peyer's patches are lymphoid follicles that perform critical immune sensing and surveillance functions in the gastrointestinal tract. The region beneath the Peyer's patch epithelium is referred to as the sub-epithelial dome (SED) and is enriched, with antigen presenting cells. Whole bacteria and similar sized microparticles of the gut lumen can be directly phagocytosed by specialised SED dendritic cells which migrate upwards and extend dendrites through the follicle associated epithelium. For the surveillance of soluble molecules and smaller particles the epithelium contains distinctive microfold (M) cells that appear to sample the lumen directly and transport the sampled material to underlying immune cells. Exactly how this occurs and how antigen, for example, is not degraded en route is not understood.

It is also unclear why Peyer's patch M cells avidly sample non-biological nanoparticles of ~20-250 nm diameter from the gut lumen. Nonetheless that it occurs is well demonstrated in cellular and animal models and also for humans with normal day-to-day exposure to nanoparticles from processed foods, pharmaceuticals and toothpaste.

SUMMARY OF THE INVENTION

Broadly, the present invention is based on the inventors' insight from the experiments disclosed herein that, the most abundant non-biological particle of the mammalian gastrointestinal lumen is calcium phosphate, in the form of amorphous calcium phosphate nanoparticles. Both $Ca^{2+}$ and $PO_4^{3-}$ ions are actively secreted into the distal bowel lumen where calcium phosphate super-saturates and thus precipitates. The secretion of calcium by the gut is often referred to as endogenous losses, but why this should occur is not known, as it contributes little to the homeostasis of calcium, the excretion of which is mediated through urine. The present invention is further based on the inventors' findings that in the gastrointestinal tract, calcium ions and phosphate ions precipitate and form nanoparticles and small microparticles that trap organic molecules present in the lumen for delivery to gut mucosal immune cells in Peyer's patches and to the mesenteric lymph nodes. Without wishing to be bound by any particular theory, the present inventors believe that this contributes to gut immunosurveillance of antigens and other molecules that are in the local environment, providing a mechanism by which the antigens and other molecules are presented to or seen by the immune system. The studies disclosed herein demonstrate that this occurs naturally for bacterial peptidoglycan in experiments in which sections of marine and human intestinal tissue were used for detecting the presence of calcium phosphate nanoparticles and the presence of peptidoglycan, together, in specialist gut immune cells. This is also confirmed by showing in mice that orally fed protein antigen, namely ovalbumin, follows this pathway.

Whilst it has been widely proposed that microparticulate, that is to say micrometre diameter sized or at least of a typical microbe size, calcium phosphate may form and have function in the intestinal tract, the present invention concerns smaller amorphous particles. The present inventors have further shown that the endogenously produced calcium phosphate nanoparticles comprise an amorphous calcium phosphate phase typically 75 nm to 150 nm in diameter, albeit as small as 5 nm and as large as 250 nm, and that they have extensive porosity by electron microscopy. The porosity is typically 1-2 nm in diameter and is proposed to be in part or whole due to incorporation of organic molecules that cannot be imaged by electron microscopy.

The present inventors realised that the uptake of endogenous small nanoparticles by immune cells in the gastrointestinal tract means that synthetic mimetics of endogenous nanoparticles might be developed which are capable of transporting cargo material, such as cargo molecules or nanoparticles, for uptake by cells in a manner analogous to the endogenously produced nanoparticles. Accordingly, in one aspect, the present invention relates to synthetic mimetics of the small endogenous amorphous calcium phosphate nanoparticles and their uses, in particular for trapping and delivering biologically active cargo materials, such as cargo molecules and/or nanoparticles, for use in both therapeutic and diagnostic applications. Accordingly, in this aspect, the present invention relates to a composition comprising amorphous magnesium-substituted calcium phosphate (AMCP), wherein the amorphous magnesium-substituted calcium phosphate entraps a biologically active cargo material for delivery to a site of interest. In a related aspect, the present invention provides amorphous magnesium-substituted calcium phosphate compositions for use in delivering cargo materials, wherein the amorphous magnesium-substituted calcium phosphate entraps a cargo material for use in therapy. In a related aspect, the present invention provides amorphous magnesium-substituted calcium phosphate compositions for use in delivering cargo materials, wherein the amorphous magnesium-substituted calcium phosphate entraps a cargo material for use in a method of diagnosis using the cargo material and related methods.

In a related aspect, the present invention provides a composition for use in a method of treating or preventing a condition by delivering a biologically active cargo material to the gastrointestinal tract, wherein the composition comprises amorphous magnesium-substituted calcium phosphate (AMCP) which entraps the biologically active cargo material, thereby enabling the cargo material to be delivered to a site of interest in the gastrointestinal tract.

In a further aspect, the present invention provides a method of treating or preventing a condition by delivering a biologically active cargo material to the gastrointestinal tract, the method comprising administering to a subject in need of treatment a composition comprising amorphous magnesium-substituted calcium phosphate (AMCP) which entraps the biologically active cargo material, thereby enabling the cargo material to be delivered to a site of interest in the gastrointestinal tract.

In a further aspect, the present invention provides a composition for use in a method of treating or preventing inflammatory bowel diseases, such as Crohn's disease or coeliac disease, by delivering a biologically active cargo material to the gastrointestinal tract, wherein the composition comprises amorphous magnesium-substituted calcium phosphate (AMCP) which entraps the biologically active cargo material, thereby enabling the cargo material to be delivered to a site of interest in the gastrointestinal tract.

In a further aspect, the present invention provides a composition for use in a method of treating or preventing an autoimmune disease, by delivering a biologically active cargo material to the gastrointestinal tract, wherein the composition comprises amorphous magnesium-substituted calcium phosphate (AMCP) which entraps the biologically active cargo material, thereby enabling the cargo material to be delivered, to a site of interest in the gastrointestinal tract. Examples of autoimmune diseases include multiple sclerosis, coeliac disease, type 1 diabetes and Systemic Lupus Erythematosis (SLE).

In a further aspect, the present invention provides a composition for use in a method of treating or preventing allergy by delivering a biologically active cargo material to the gastrointestinal tract, wherein the composition comprises amorphous magnesium-substituted calcium phosphate (AMCP) which entraps the biologically active cargo material, thereby enabling the cargo material to be delivered to a site of interest in the gastrointestinal tract.

In a further aspect, the present invention provides a composition for use in a method of treating or preventing cancer by delivering a biologically active cargo material to the gastrointestinal tract, wherein the composition comprises amorphous magnesium-substituted calcium phosphate (AMCP) which entraps the biologically active cargo material, thereby enabling the cargo material to be delivered to a site of interest in the gastrointestinal tract. Examples of medical uses of the present invention relating to the treatment or prevention of cancer, for example Myeloid Leukaemia, such as Chronic Myelogenous Leukaemia (CML), Acute Lymphoblastic Leukaemia and Acute Myelogenous Leukaemia (AML).

In a further aspect, the present invention provides a method of delivering a biologically active cargo material to a cell, the method comprising contacting the cell with a composition comprising the biologically active cargo material entrapped in amorphous magnesium-substituted calcium phosphate (AMCP) so that the composition disperses to form nanoparticles that are capable of being taken up by the cells, thereby delivering the biologically active cargo material to the cell.

In a further aspect, the present invention provides a process for producing amorphous magnesium-substituted, calcium phosphate compositions that contain entrapped biologically active cargo material, the process comprising:

(a) providing a solution comprising calcium ions ($Ca^{2+}$), magnesium ions ($Mg^{2+}$) and a solution comprising phosphate ions ($PO_4^{2-}$), wherein one or both of the solutions comprise one or more biologically active cargo materials;

(b) mixing the solution comprising calcium ions ($Ca^{2+}$), magnesium ions ($Mg^{2+}$) with the solution comprising phosphate ions ($PO_4^{2-}$) to precipitate amorphous magnesium-substituted calcium phosphate in which the biologically active cargo materials are entrapped;

(c) recovering the amorphous magnesium-substituted calcium phosphate; and (d) optionally washing and drying the amorphous magnesium-substituted calcium phosphate.

The present inventors have found that after synthesis, the amorphous magnesium-substituted calcium phosphate comprise aggregated nanoparticles that are capable of dispersing to deliver the biologically active cargo molecule to the site of interest. This has the advantage that the materials form nanoparticles in biological environments for the delivery of the cargo, while being easy to purify and process after synthesis. Advantageously, the amorphous magnesium-substituted calcium phosphate compositions disperse efficiently in aqueous environments in the presence of protein, adapting them to delivery of the cargo material in in vivo settings.

In some applications, the present inventors found that the amorphous magnesium-substituted calcium phosphate compositions of the present invention have the significant advantage that they are a silent delivery platform that does not cause an adjuvant and/or a direct transcriptional response to the nanoparticles at the site of interest. For example, cells that have taken up and processed the nanoparticles do not have a response that differs substantially to the response to the biologically active cargo material alone and/or to unchallenged control cells.

Accordingly, in some instances, the amorphous magnesium-substituted calcium phosphate nanoparticles are silent in the sense of not modulating a direct transcriptional response that differs between cells challenged with the nanoparticles and unchallenged control cells, preferably as assessed within 3 hours of exposure to the amorphous magnesium-substituted calcium phosphate nanoparticles. This may be determined in an experiment based on FIG. 10 in which it was shown that this correlation in the direct transcriptional response of genes to the synthetic AMCP compared to normal cells preferably falls within a range of two-fold up and two-fold down regulation.

This feature distinguishes the compositions of the present invention from prior art delivery systems where the material from which the delivery agent is formed produces an adjuvant response in addition to the response caused, by a delivered antigen. In some embodiments, the amorphous magnesium-substituted calcium phosphate compositions of the present invention can be used to target delivery of the cargo molecules to cell types that preferentially take up the nanoparticles. By way of illustration, this includes cells in the gastrointestinal tract such as the antigen presenting immune cells of intestinal lymphoid follicles. The cell types that preferentially take up the nanoparticles include antigen presenting B cells but are especially dendritic cells and macrophages, such as CD11b and CD11c positive cells.

Alternatively or additionally, the present inventors further found that the amorphous magnesium-substituted calcium phosphate compositions of the present invention have the significant advantage that the compositions are stabilised in an amorphous phase by the magnesium ions and/or the biologically active cargo material. In this connection, in the field of inorganic chemistry, it has been recognised that substitution of $Ca^{2+}$ ions in ACP by $Mg^{2+}$ ions leads to greater stability of the amorphous state, lessening its tendency to convert, through to more crystalline phases. Boskey & Posner (1973, 1974) showed that, at a ratio of at least 1:25 (Mg:Ca), an amorphous Mg Ca $PO_4$ phase could be produced which, as a dry powder, remains stable over time. However, the present, inventors recognised for the first time that during its synthesis, amorphous calcium phosphate stabilized by magnesium ions (AMCP) is especially useful to trap a wide range of cargo materials, including cargo molecules, such as protein antigens, bioactive cytokines, peptidoglycans, low molecular weight organic molecules, and cargo nanoparticles, such as inorganic nanoparticles. This in turn opens up a range of different applications for the amorphous magnesium-substituted calcium phosphate compositions of the present invention. Specific examples of cargo molecules include, but are not limited to, muramyl dipeptide (MDP), lipopolysaccharides (LPS), polyinosinic: polycytidylic acid (Poly I:C) and retinoic acid (RA).

In addition, the present inventors found that the synthetic processes of the present invention may be used to form amorphous magnesium-substituted calcium phosphate compositions (Mg, Ca, $PO_4$) in which the cargo molecules associated with the composition is at least partially incorporated within the material, rather than simply being bound, to the surface of particles. This means that the amorphous magnesium-substituted calcium phosphate composition templates around the cargo material to some extent giving the appearance of the formation of porous materials overall. In other words, by co-precipitating the amorphous magnesium-substituted calcium phosphate compositions in the presence of other cargo materials, leads to at least some of these other cargo materials becoming entrapped in the material during the synthesis. Advantageously, this may better protect the cargo en route to the target cell in vivo compared to if the cargo were only adsorbed to the surface.

Moreover, the present invention demonstrates that amorphous magnesium-substituted calcium phosphate compositions of the present invention are capable of dispersing to form nanoparticles containing cargo materials that are amenable to uptake by cells, leading to the release of the cargo materials upon cellular digestion, and consequently providing a typical cellular response to the cargo material. For example, bacterial peptidoglycan may be trapped by amorphous magnesium-substituted calcium phosphate compositions and, when delivered to cells, will yield the production of cytokines (IL-10; IL-I; TNFα etc.) typical of bacterial peptidoglycan. As stated, above, the present inventors surprisingly found that the particle-embedded cargo faithfully recapitulates the cellular signals derived from the cargo alone, i.e. there is no attenuation of signalling in either direction.

Advantageously, the amorphous magnesium-substituted calcium phosphate nanoparticles are non-toxic and safe for uptake by cells. It is generally recognised in the art that amorphous particles are safer for cells than crystalline particles. Cells which are exposed to and take up the nanoparticles of the present invention do not die, unlike with protracted exposure to the calcium phosphate hydroxyapatite, for example.

Moreover, the amorphous magnesium-substituted calcium phosphate compositions of the present invention may be used to co-deliver two or more different cargo material. For example, the experiments described herein have shown that if peptidoglycan and antigen are both present, then the ensuing T cell response to the antigen is significantly reduced due to IL-10 being secreted due to the presence of the peptidoglycan.

In a further aspect, the present invention is based on the observation that the cells that endogenous amorphous calcium phosphate nanoparticles are associated with in the gut show reduced expression or the absence of the protein programmed death ligand one (PD-L1) in Crohn's disease, that is otherwise present in the corresponding healthy cells. PD-L1 is a tolerance-inducing molecule which implies that the cause of the disease may be related to the failure of these cells to express PD-L1. Accordingly, in this aspect, the present invention provides an agent for use in a method of treating inflammatory bowel disease, such as Crohn's disease, wherein the agent has the property of (a) up-regulating the expression of PD-L1; or (b) activating PD-L1 protein; or (c) inhibiting repression of PD-L1 expression; or (d) otherwise activating PD-L1 on some antigen presenting cells of the intestinal lymphoid follicles. In related aspects, the present invention provides a pharmaceutical composition which comprises such an agent, wherein the agent is entrapped as a cargo material within an amorphous magnesium-substituted calcium phosphate material of the present invention.

In a further aspect, the present invention provides an agent capable of promoting PD-L1 expression in antigen presenting immune cells of intestinal lymphoid follicles for use in a method of treating Crohn's disease.

Embodiments of the present invention will now be described by way of example and not limitation with reference to the accompanying figures. However various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

showing internalised AMCP (green) and induced or lack of PD-L1 (red) in health and disease, respectively.

Figure 9:
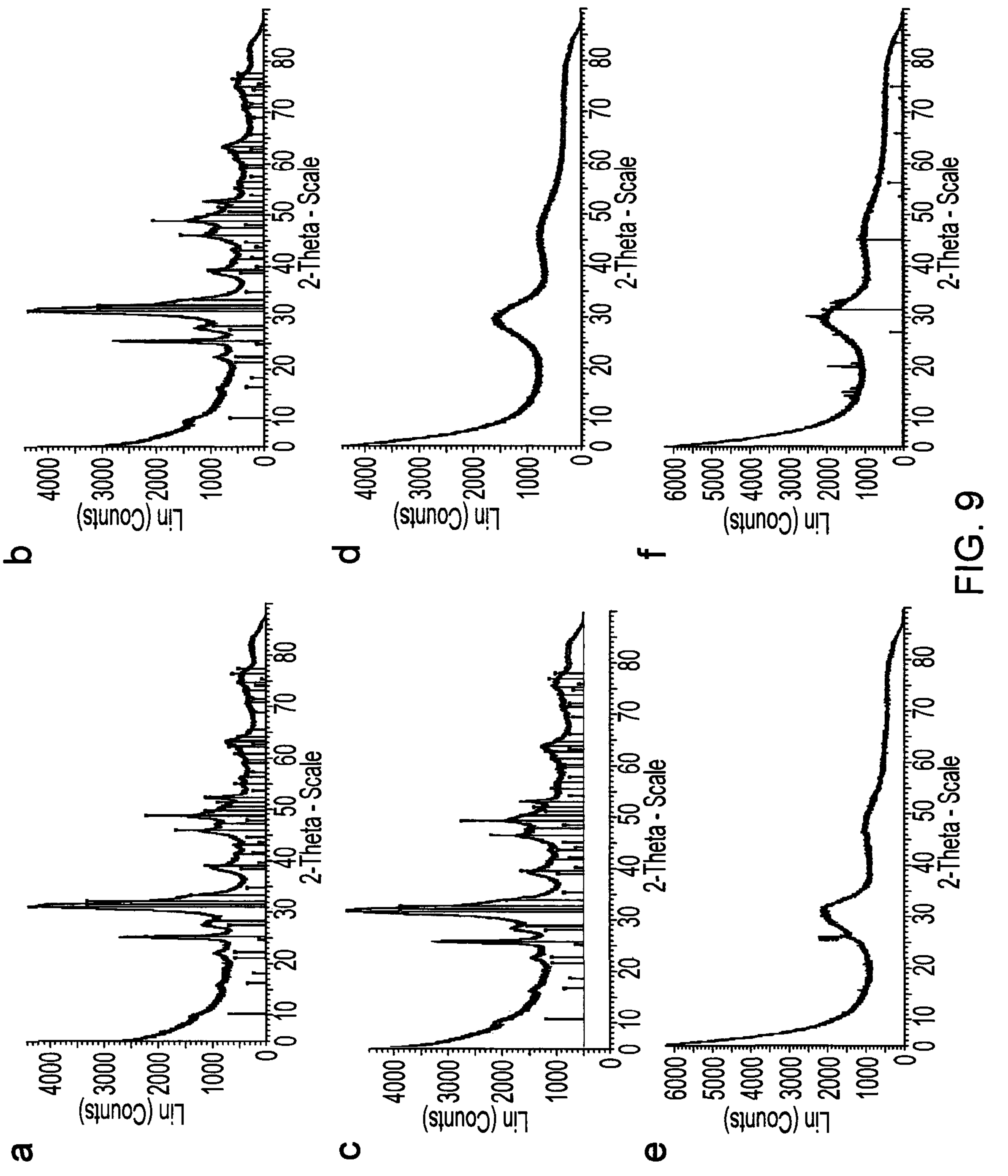

FIG. 9. X-ray diffraction patterns of calcium, phosphate nanoparticles prepared in (a) the absence of both, magnesium (Mg) and bovine serum albumin (BSA), (b) in the presence of 0.9 mM (Mg; final concentration), (c) 1.8 mm Mg, (d) 1.8 mm Mg and BSA, (e) 3.6 mM Mg and (f) 3.6 mM Mg and BSA.

Figure 10:
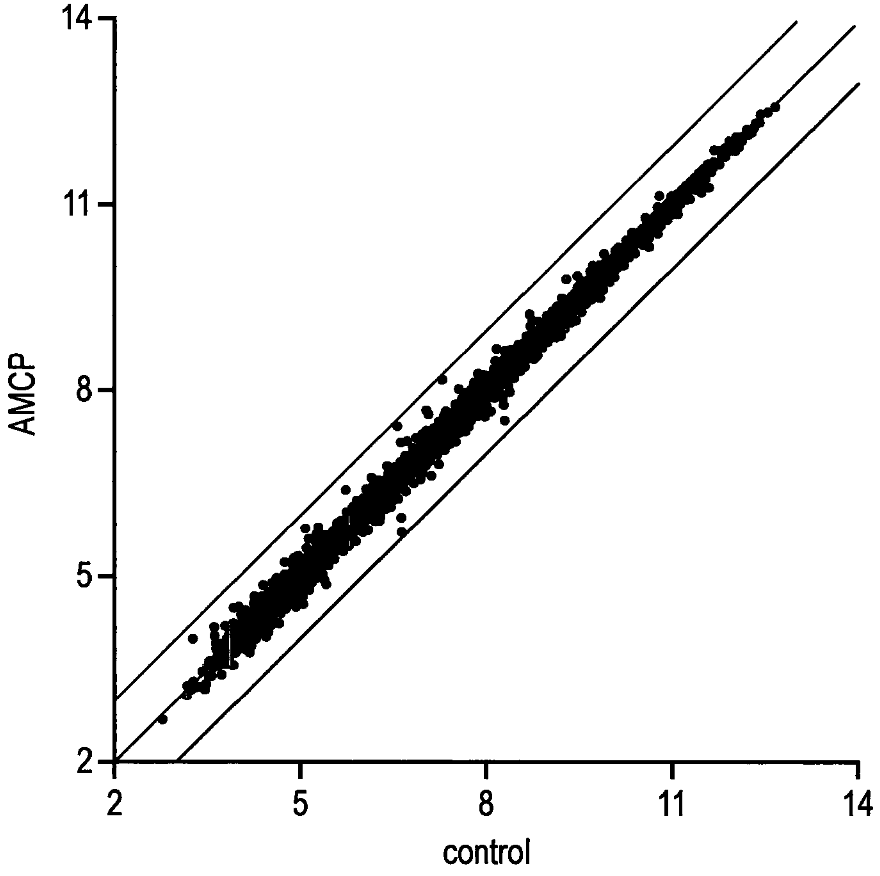

FIG. 10. Average log 2 expression values of genes, after 3 h exposure to synthetic AMCP, correlated against those of vehicle control treatment (n=7) and demonstrating that, cells challenged with protein-loaded synthetic AMCP nanoparticles displayed a similar transcriptomic 'signature' to that of unchallenged (control) cells. Theoretical line of perfect correlation is shown in the central line while the bordering lines correspond to twofold up- and down-regulation.

Figure 11:
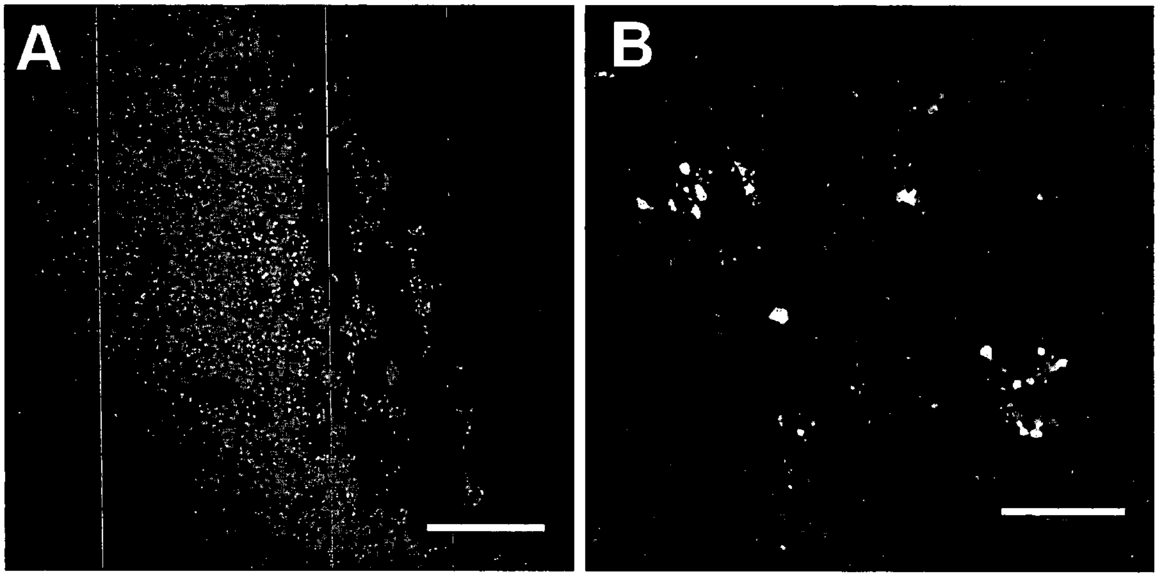

FIG. 11. A—Caecal patch displaying evident calcein staining (green) in the sub-epithelial area indicating that, in addition to Peyer's patches, immune-active lymphoid patches of the appendix also take up the endogenous nanomineral. Nuclei are shown in grey; Scale bars 50 μm. B—Murine mesenteric lymph nodes showing significant numbers of AMCP (green) nanomineral+ cells.

DETAILED DESCRIPTION

Amorphous Calcium Phosphate

Amorphous Calcium Phosphate (ACP) is unique among all forms of calcium phosphate in that it lacks long-range, periodic atomic scale order of crystalline calcium phosphates. This means that ACP can be recognised from its broad and diffuse X-ray diffraction pattern with a maximum at 25 degrees 2 theta, and no other different features compared, with well crystallized hydroxyapatite. Additionally or alternatively, amorphous calcium phosphates may be characterised as calcium phosphate materials in which analysis by XRD shows the typical broad band peaking at approximately 31 2-theta and extending from 22 to 36 2-theta (e.g. diffractograms d-f in FIG. 9). Note that this broad, band is distinct from the much sharper peak at 32 2-theta which is present, in hydroxyapatite materials (e.g. diffractograms a-c in FIG. 9). The broad XRD band is also characteristic of the amorphous magnesium-substituted calcium phosphate compositions of the present invention as shown in FIG. 9. In contrast, the XRD diffraction patterns for the at least partially crystalline materials of Dasgupta et al. and Chowdhur et al (supra) more closely resemble those of hydroxyapatite. The comparison of the X-ray diffraction patterns for amorphous calcium phosphate and crystalline hydroxyapatite is shown in FIG. 9 and the skilled person can readily determine whether a form of calcium phosphate is amorphous by X-ray diffraction, by comparing the patterns with those shown in FIG. 9. Under electron microscopy, the morphological form of ACP is shown as small spheroidal particles in the scale of tenths of nanometer. Accordingly, as used herein, ACP and AMCP ("amorphous magnesium substituted calcium phosphate") refer to such amorphous forms of calcium phosphate and do not include crystalline forms of calcium phosphate, such as hydroxyapatite.

In general, the present inventors have found that when the amorphous magnesium-substituted calcium phosphate compositions of the present invention are synthesized, they are produced in the form of agglomerated particles that are amenable to purification, for example by filtration and/or centrifugation, and processing using other techniques, such as drying and formulating the materials in compositions for storage and use. It will be apparent to those skilled in the art that an appropriate excipient may be added to the formulation to minimise or prevent aggregation during drying or other manufacturing processes. However, the present inventors have advantageously found that when the amorphous magnesium-substituted calcium phosphate compositions are delivered in an aquated environment that would exist clinically or in a biological environment, that the materials re-disperse in the form of nanoparticles having the characteristics described herein. This means, for example, that the nanoparticles have a size compatible with cellular uptake. Accordingly, as used herein, "an agglomerate" refers to a relatively loosely bound collection of particles, which are capable of re-dispersing into the individual particles, such as nanoparticles, in response to changing environment.

Preferably, the amorphous magnesium substituted calcium phosphate compositions employed in the present invention have the following characteristics. Preferably, the ratio of Mg to Ca in the amorphous magnesium-substituted calcium phosphate compositions is at least 1:25, optionally at least 1:20, optionally at least 1:10, optionally at least 1:5, optionally at least 1:4 and most optionally at least 1:3.

Generally, when the amorphous magnesium-substituted calcium, phosphate compositions are in aquated form, for example upon delivery, they disperse to form compositions of nanoparticles. Generally, the nanoparticles have mean diameters within the size range of 5 nm to 500 nm diameter, mean diameters in a range between 20 nm and 350 nm, more preferably mean diameters in a range between 20 nm and 200 nm, more preferably mean diameters in a range between 20 nm and 150 nm, more preferably mean diameters in a range between 75 nm and 150 nm. Within a given size range, it is preferred that at least 75% of the nanoparticles of amorphous magnesium-substituted calcium phosphate have an average diameter in the range, and more preferably that at least 90% of the nanoparticles of amorphous magnesium-substituted calcium phosphate have an average diameter in the range. Particle size may be assessed, by Nanoparticle Tracking Analysis, for example using a Nanosight NS500 (Nanosight, Amesbury, UK) using NTA2.2 Analytical Software.

As explained, below, the amorphous magnesium substituted calcium phosphate compositions of the present invention appear porous as they have entrapped or templated around the cargo materials such as cargo molecules or cargo nanoparticles. The porosity of the amorphous magnesium-substituted calcium phosphate compositions represents a combination of true pores and pores partially or totally containing organic cargo for which the electron microscope is 'blind' as it shows regions of mineral and their holes being regions (pores) of non-mineral. This can be observed by TEM, better by STEM and best by STEM tomography. BET or mercury intrusion can provide measures of the true pores that are not occupied by cargo. Typically, the size of the pores in the nanoparticles are 10 nm or less, more preferably 5 nm or less, and most preferably about 1-3 nm. Generally, when they are in the form of nanoparticles, the amorphous magnesium-substituted calcium phosphate particles are approximately spheroidal or elongated spheroidal in shape.

The stability of the amorphous magnesium-substituted calcium compositions of the present invention is a key advantage of the materials of the present invention and this arises, in part, from, the presence of magnesium ions in the material. Amorphous AMCP (Mg Ca $PO_4$) phase could be produced which, as a dry powder, remains stable over time. Preferably, this contains at least one Mg atom for every 25 Ca atoms and no more than one Mg ion for every one Ca ions. More preferred Mg:Ca ratios are at least 1:20, more preferably at least 1:10 and more preferably at least 1:5 Mg:Ca ions, more preferably at least 1:4 Mg:Ca ions or at least 1:3 Mg:Ca ions.

Computational Modelling of Magnesium Substituted Calcium Phosphate Nanoparticles First principles DFT modelling was undertaken using the CASTEP (Clark et al: First principles methods using CASTEP. Zeitschrift für Kristaliographie: 220 (5-6): 567-570, 2005) plane-wave simulation code. Small precursor calcium phosphate clusters, representative of the early stages of particle nucleation, were constructed and simulated.

Posner's cluster (Posner, Acc. Chem. Res., 8: 273-281, 1975), $(Ca_9(PO_4)_6$, is considered to be a precursor to the formation of crystalline apatite. This structure was used as a starting model but the formula was changed to reflect an experimentally measured composition, $MgCa_7(PO_4)_6$. Analysis of the clusters' geometric structure and stability were carried out. The stability was assessed in thermodynamic terms, using formation energy analysis. This analysis led to the following results. At the experimentally measured composition above, the cluster is more stable with magnesium than with calcium. This is not true of Posner's cluster, where the magnesium, substitution in not favourable.

To make a magnesium substitution in crystalline hydroxyapatite (HA), energy is required and hence the formation energy of the substitution is positive. The formation energy of the same substitution in the experimentally measured composition cluster is negative, and hence more favourable. This shows that magnesium in the experimental cluster stabilizes the amorphous structure against crystallisation. The most favourable position for the magnesium, substitution is at the very centre of the cluster. This is the position where the magnesium ion is most stable.

The geometry of the cluster is much "looser" when compared to both the substituted Posner's cluster and the cluster without magnesium. Compared to a substituted Posner's cluster, the Mg—P distance in 2.5% larger and the P—P distance 5% larger. The cluster loses its spherical geometry, showing a more amorphous looking cluster with weaker bonding.

Trapped Cargo Material

Experiments described herein show that it is possible to trap one or more cargo materials in the amorphous magnesium-substituted calcium phosphate compositions of the present invention.

Nanoparticles as Cargo Materials

Nanoparticle structures may have therapeutic benefit either directly themselves or due to the carriage of a therapeutic within. Small nanoparticles, generally <20 nm, preferably <15 nm and most preferably <10 nm in diameter may be readily incorporated in the amorphous magnesium-substituted calcium compositions of the present invention. This may have the advantage of targeting the small nanoparticles to where, otherwise, they would not be directed. For example, interfering RNA for pandemic flu may be incorporated in small nuclear-targeted nanoparticle which itself is incorporated in an amorphous magnesium-substituted calcium composition to allow initial upper airways delivery by inhaler or similar device and enabling the amorphous magnesium-substituted calcium composition to dissolve in lung lining fluid before releasing the smaller-particles for further travel and delivery to deeper epithelial cells.

A second example is therapeutic iron. For example, it may be desirable to bypass or reduce gastric degradation. An example of this is nanoparticulate iron hydroxides like the ferritin core that one may wish to deliver to the small intestine intact so that they are taken up whole in the small intestine through endocytosis and then dissolve intralysosomally for Fe utilisation.

In other aspects, the present invention allows the delivery of metal nanoparticles or metal oxo-hydroxide nanoparticles, such as iron or copper nanoparticles, or quantum dots using the amorphous magnesium-substituted calcium compositions, which may be desirable for experimentation for example, allowing the particle's cargo to be tracked, both in in vitro and in vivo systems. Accordingly in a further aspect, the present, invention provides a composition for use in a method of diagnosis comprising amorphous magnesium-substituted calcium phosphate (AMCP) which entraps a cargo material comprising a detectable moiety, such as a label. In one embodiment, this may involve delivering a cargo material to the gastrointestinal tract, thereby enabling the cargo material, to be delivered to a site of interest, in the gastrointestinal tract and detected using a technique capable of detecting the detectable moiety.

In a related aspect, the present invention provides a method of diagnosis which comprises administering to a subject a composition comprising amorphous magnesium-substituted calcium phosphate (AMCP) which entraps a cargo material comprising a detectable moiety, delivering the amorphous magnesium-substituted calcium phosphate comprising the cargo material to the gastrointestinal tract, and detecting the detectable moiety.

Vaccines as Cargo Materials

Therapeutics may require a) targeting to a specific cell type and/or b) to be protected from digestion during gastrointestinal transit. The amorphous magnesium-substituted calcium phosphate composition of the present invention may offer advantages in both cases. First by targeting APCs and/or reticulo-endothelial cells whether given orally, rectally or parenterally. For the reasons set out herein, amor-

| | Total weight (mg) | Organic material (μg) | Starting Ca:P:M (n = 2) | Synthesis Ca:P:Mg (n = 2) | Synthesis Ca/P molar ratio (n = 2) | Synthesis (Ca + Mg)/P molar ratio (n = 2) |
|---|---|---|---|---|---|---|
| AMCP | 2.19 | — | 1:1.3:0.26 | 1:0.9:0.16 | 1.11 | 1.29 |
| AMCP/Avidin | — | 157.8 | — | — | — | — |
| AMCP/BSA | 2.39 | 242.9 | 1:1.25:0.25 | 1:0.9:0.16 | 1.11 | 1.29 |
| AMCP/BSA/PGN | 1.98 | 315.7 | 1:1.27:0.25 | 1:0.98:0.17 | 1.02 | 1.19 |
| AMCP/BSA/sPGN | — | 245.8 | — | — | — | — |
| AMCP/BSA/Starch | — | 46.0 (Starch) | — | — | — | — |
| AMCP/BSA/PPD | — | 240.5 | — | — | — | — |
| AMCP/BSA/TSLP | — | $\leq 1.4.10^{-3}$ (TSLP) | — | — | — | — |

phous magnesium-substituted calcium composition of the present invention are well suited to delivery of cargo materials to the Peyer's patches and to Mesenteric Lymph Nodes (MLN). Secondly, by providing some protection to digestion from enzymes. An example would be vaccination. The vaccine, which comprise one or more one cargo molecules, may be incorporated in amorphous magnesium-substituted calcium compositions to achieve both or one of the goals above. A second example is therapeutic delivery in inflammatory bowel disease, rheumatoid arthritis or other inflammatory or autoimmune disorders. It may be beneficial for a specific therapeutic such as steroid, methotrexate, azathioprine or even 'biologicals' that are used as non-targeted therapies to in fact be packaged in amorphous magnesium-substituted calcium compositions of the present invention and targeted to APCs and related cells.

Without wishing to be bound by any particular theory, the present inventors believe that amorphous magnesium-substituted calcium phosphate compositions may be used to treat conditions such as autoimmune conditions, inflammatory bowel disease, rheumatoid arthritis or other inflammatory disorders by inducing oral tolerance to dampen systemic and/or local responses that underlie these conditions. While orally consumed, materials that have not been digested, may be trapped, by endogenously produced calcium phosphate nanoparticles and carried to relevant cells, this process is relatively inefficient compared to the cellular exposure to a cargo material already present, in the synthetic amorphous magnesium-substituted calcium phosphate compositions of the present invention.

Nucleic Acid Cargo Molecules

The amorphous magnesium-substituted calcium phosphate compositions may be used to deliver cargo material that is nucleic acid sequences, for example to obtain expression of the nucleic acid sequence in a cell, delivery of short nucleic acid sequences for gene knock down and so on. Generally, the nucleic acid may be a naked sequence or else incorporated into an expression vector. Nucleic acid may be wholly or partially synthetic and may include genomic DNA, cDNA or RNA. Where nucleic acid according to the invention includes RNA, reference to the sequence shown should be construed, as reference to the RNA equivalent, with U substituted for T.

Nucleic acid sequences, for example encoding all or part of a gene and/or its regulatory elements can be readily prepared by the skilled person using the information and references contained herein and techniques known in the art (for example, see Sambrook, Fritsch and Maniatis, Molecular Cloning, A Laboratory Manual, Cold Spring Harbour Laboratory Press, 1989, and Ausubel et al, Short Protocols in Molecular Biology, John Wiley and Sons, 1992). These techniques include (i) the use of the polymerase chain reaction (PCR) to amplify samples of such nucleic acid, e.g. from genomic sources, (ii) chemical synthesis, or (iii) amplification in *E. coli*. Modifications to the nucleic acid sequences can be made, e.g. using site directed mutagenesis, to take account of codon preference in the host cells used to express the nucleic acid. PCR techniques for the amplification of nucleic acid are described in U.S. Pat. No. 4,683,195. References for the general use of PCR techniques include Mullis et al, Cold Spring Harbour Symp. Quant. Biol., 51:263, (1987), Ehrlich. (ed.), PCR Technology, Stockton Press, N.Y., 1989, Ehrlich et al, Science, 252:1643-1650, (1991), "PCR protocols; A Guide to Methods and Applications", Eds. Innis et al, Academic Press, New York, (1990).

In order to obtain expression of a nucleic acid sequence, it can be incorporated in a vector having control sequences operably linked to the nucleic acid to control its expression. The vector may include other sequences such as promoters or enhancers to drive the expression of the inserted nucleic acid, nucleic acid sequences so that the polypeptide encoded by the gene is produced as a fusion and/or nucleic acid encoding secretion signals so that the polypeptide produced in the host cell is secreted from the cell. Suitable vectors can be chosen or constructed, containing appropriate regulatory sequences, including promoter sequences, terminator fragments, polyadenylation sequences, enhancer sequences, marker genes and other sequences as appropriate. Vectors may be plasmids or viral, e.g. 'phage, or phagemid, as appropriate. For further details see, for example, Molecular Cloning: a Laboratory Manual: 2nd edition, Sambrook et al., 1989, Cold Spring Harbour Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et. al. eds., John Wiley & Sons, 1992. The nucleic acid or expression vectors may be transfected into target cells using the nanoparticles into which the amorphous magnesium-substituted calcium phosphate compositions of the present invention disperse in use so that the nucleic acid encoding a gene of interest is expressed in the target cells.

Polypeptide Cargo Molecules

The amorphous magnesium-substituted calcium phosphate nanoparticles may be used, to deliver cargo molecules that are peptides or polypeptides, for example protein antigens or cytokines. Polypeptides as used herein includes polymers in which the monomers are amino acids and are joined together through amide bonds. The amino acids forming polypeptides may include unnatural amino acids, such as β-alanine, phenylglycine and homoarginine, or amino acids that are not nucleic acid-encoded, and/or amino acids that have been modified to include reactive groups, glycosylation sites, polymers, therapeutic moieties, biomolecules and the like may also be used in the invention. All of the amino acids used in the present invention may be either the D- or L forms. The use of the naturally occurring L-isomer is generally preferred.

The methods described are applicable to any size or type of polypeptide from single amino acids and peptides to polypeptides and proteins having molecular weights of up to or over 100 kDa, and in exceptional cases, such as ferritin, of up to or exceeding 1 million kDa. Accordingly, while for convenience, the methods herein are generally described by reference to "polypeptides", this should be taken to include shorter sequences of amino acids (e.g., from 2, 3, 4, 5 or 10 amino acids in length to 30, 40 or 50 amino acids in length), sometimes referred, to in the art as peptides, as well as to larger polypeptides generally referred to as proteins. The term should also be taken to include polypeptides having secondary, tertiary or quaternary structure generally referred to as proteins, as well as multi-domain proteins or other critical proteins and polypeptides in disease process.

Examples of suitable classes of polypeptides include interferons, interleukins, chemokines, lymphokines and cytokines, for example for conditioning and cell-re-education, allergens (i.e. oral or systemic), bacterial proteins and autoimmune proteins.

Microbial-Associated Molecular Patterns Cargo Molecules

The amorphous magnesium-substituted calcium phosphate compositions may be used to deliver cargo molecules that encompass microbial-associated molecular patterns (MAMPs), such as peptidoglycans. Examples of MAMPs include lipopolysaccharides, muramyl dipeptide, lipotocheic acids or any molecules that can engage the cellular toll-like receptors and/or intra-cellular SOD-like receptors and associated family members. MAMPs can be used for either their inflammatory (adjuvant) or anti-inflammatory properties (tolerogenic) depending on the cell environment. For example in the gastrointestinal tract the default is one of tolerance. In the periphery, it is one of immune responsiveness. It is known in the art that in culture cells can be conditioned to try and mimic their gut immuno-tolerant state. Peptidoglycan may be delivered into target cells, in vivo or ex vivo with appropriate conditioning, using the amorphous magnesium-substituted calcium phosphate compositions of the present invention so that tolerogenic signals are induced in the cell of interest. For example, IL-10 may be secreted and PD-L1 up-regulated. If additionally the particle carries an antigen then the T cell response to the presented antigen may be usefully tolerogenic. In conditions such as Crohn's disease where this pathway may not be operational, other materials could be considered as discussed further elsewhere herein.

Small Molecules as Cargo Molecules

The amorphous magnesium-substituted calcium phosphate compositions may be purposefully used to trap and deliver small molecules such as nutrients. This may have benefit in a number of ways. Firstly, for nutrients that are synergistic with the nutritional benefit of calcium especially magnesium, silicon and Vitamin D. Secondly, the amorphous magnesium-substituted calcium phosphate compositions may act to partially or wholly protect the nutrient from digestion by the nanoparticles into which the compositions of the present invention disperse by dissolving in the stomach and thus delaying the time that gastric acid has to act on the nutrient composition inside. A further example involves the targeted delivery of small molecules such as nutrients, amino acids, nucleic acids, including their sequences to cells that specifically scavenge the AMCP particles whether administered orally or parenterally. APCs and reticulo-endothelial cells would be especially targeted in this fashion.

Synthesis of Amorphous Magnesium-Substituted Calcium Phosphate Materials

The synthesis of the amorphous magnesium-substituted calcium phosphate materials of the present, invention containing entrapped biologically active cargo materials was adapted from the methods disclosed, by Boskey and Posner (1973, 1974), with the distinction that their materials did not entrap biologically active cargo material, and with some further improvements to their methods. Broadly, the process of the present invention employs magnesium ions ($Mg^{2+}$) to stabilize calcium phosphate in the amorphous phase. However, the present inventors have found that the biologically active cargo materials may provide additional stabilization beyond that, provided by the magnesium ions ($Mg^{2+}$) and that the efficiency of the step of drying the precipitated, materials plays an important role in preserving the amorphous phase.

Accordingly, in one aspect, the present invention provides a process for producing amorphous magnesium-substituted calcium phosphate compositions that contain entrapped biologically active cargo material, the process comprising:

(a) providing a solution comprising calcium ions ($Ca^{2+}$), magnesium ions ($Mg^{2+}$) and a solution comprising phosphate ions ($PO_4^{2-}$), wherein one or both of the solutions comprise one or more biologically active cargo material;

(b) mixing the solution comprising calcium ions ($Ca^{2+}$), magnesium ions ($Mg^{2+}$) with the solution comprising phosphate ions ($PO_4^{2-}$) to precipitate amorphous magnesium-substituted calcium phosphate in which the biologically active cargo material, is entrapped;

(c) recovering the amorphous magnesium-substituted calcium phosphate; and (d) optionally washing and drying the amorphous magnesium-substituted calcium phosphate with entrapped cargo material.

Conveniently, the solution comprising calcium ions ($Ca^{2+}$), magnesium ions ($Mg^{2+}$) and biologically active cargo molecules is buffered, for example using a Tris, HEPES, BICINE, TRICINE or a citric acid buffer, or an amino acid, such as lysine or glycine, at a pH between about pH 7.5 and pH 10, and more preferably at a pH of about 8.0. This may be achieved using a Tris buffer at a concentration range of between 50 mM and 300 mM, for example at about 150 mM Tris. Generally, the concentration of calcium, ions ($Ca^{2+}$) is between 5 mM and 200 mM, for example at about 17.7 mM. Generally, the ratio of magnesium ions ($Mg^{2+}$) to calcium ions ($Ca^{2+}$) is at least 1:25, optionally at least 1:20, optionally at least 1:10, optionally at least 1:5, optionally at least 1:4 and optionally at least 1:3. The concentration of the biologically active cargo molecules depends on the amount of the molecules that, it is desired to trap in the precipitated nanoparticles. By way of illustration, in applications where the biologically active cargo molecule is a therapeutically active molecule, the concentration may be generally lower than for applications where the biologically active cargo molecule is a nutraceutical molecule.

Figure 7:
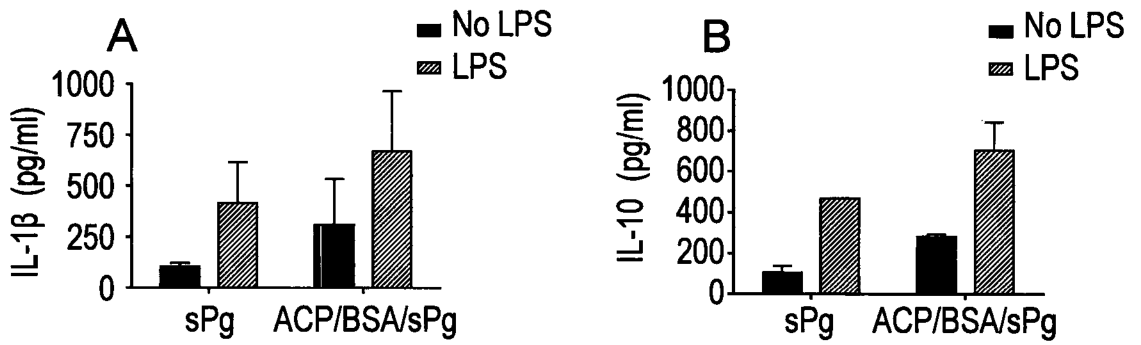
FIG. 7. IL-1β (A) and IL-10 (B) responses in PBMC that, were stimulated with or without LPS (3 hours; 10 ng/ml) and then challenged with sPg and AMCP/BSA/sPg for another 3 hours (n=2). Supernatants were analysed after 3 hours challenge and with an additional chase of 21 hours.
Figure 8:
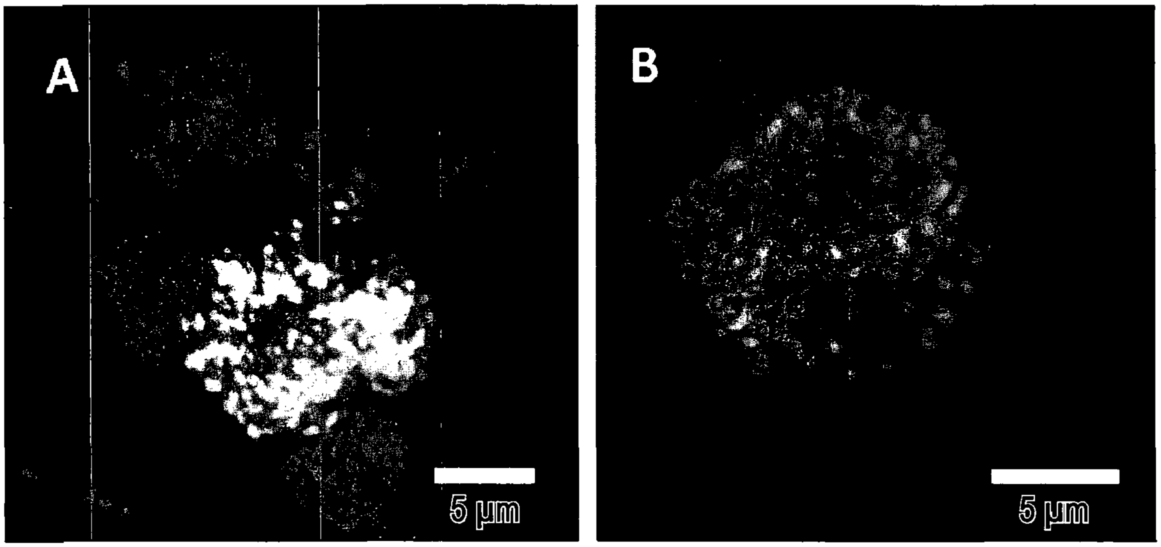
FIG. 8. Confocal micrographs of Peyer's patch intestinal cells in health (A; grey) and Crohn's disease (B; blue)

The concentration of solution of phosphate ions ($PO_4^{2-}$) is between 5 mM and 200 mM, for example at about 20 mM, and is generally buffered in the same buffer solution as the solution comprising calcium ions ($Ca^{2+}$), magnesium ions ($Mg^{2+}$) and biologically active cargo molecules. The rapid addition of the solution of phosphate ions ($PO_4^{2-}$) to a calcium solution ensure the ratios of $Ca^{2+}$ and $PO_4^{2-}$ are constant whilst the amorphous calcium phosphate (ACP) phase is formed. In the absence of stabilisers, this would normally rapidly convert, to more crystalline phases, such as hydroxyapatite. This conversion can be prevented, or at least, limited, by the addition of magnesium, ions ($Mg^{2+}$) in the synthesis which, by being incorporated in the calcium phosphate mineral, disrupts the lattice and reduces surface remodelling (FIG. 7A, B).

While the stabilisation by amorphous calcium phosphate by magnesium ions ($Mg^{2+}$) was first investigated by Boskey & Posner (1974), the present inventors have surprisingly found that, the porous structure of the nanoparticles is capable of incorporating a range of different types of biologically active cargo molecules. In addition, the present inventors found that the cargo molecules entrapped within the structure of the nanoparticles further increases the stabilisation of the amorphous phase during synthesis and for subsequent drying and storage. This enables the process of the present invention to employ lower concentrations of magnesium ions ($Mg^{2+}$) than Boskey & Posner found to be necessary to stabilise the amorphous calcium phosphate phase, for example 1.8 mM Mg per 17.7 mM Ca. However, in general, higher concentrations of magnesium ions ($Mg^{2+}$) are preferred to enhance the stability of the nanoparticles thus produced.

Conveniently, the recovery of the amorphous magnesium-substituted calcium phosphate compositions of the present invention can be carried out by centrifugation or filtration, and the compositions then washed and partially or totally dried. This ease of manipulation is achieved due to transient agglomeration of the nanoparticles during synthesis to micron-sized agglomerates which will then re-disperse in nano form when appropriately re-aquated. Advantageously, the washing and drying steps may be done using one or more acetone washes to help remove water from the amorphous magnesium-substituted calcium phosphate compositions. The present inventors have found that a way of achieving this is to reslurry the compositions in acetone (preferably at a pH of about 10) and then to dry the composition using centrifugation. For optimum stabilisation of the compositions, the acetone washing step was repeated twice, see Table 1 below.

TABLE 1

Effect of Mg concentration, protein and acetone drying on the mineral phase of materials produced from 17.7 mM $Ca^{2+}$, 19.7 mM $PO_4^{2-}$ in 150 mM Tris at pH 8. Based on these findings, acetone re-slurring stabilises phase through the removal of water and, therefore, one acetone re-slurry may have an equivalent effect to two-slurrying steps provided enough water is removed from the material

| [Mg], mM | Mg:Ca Ratio at synthesis (reagents) | One acetone Reslurry Without Protein | One acetone Reslurry With Protein | Two acetone Reslurries Without Protein | Two acetone Reslurries With Protein |
|---|---|---|---|---|---|
| 0 | | Crystalline | Crystalline | Crystalline | Crystalline |
| 0.9 | 1:19.7 | Crystalline | Crystalline | Crystalline | Crystalline |
| 1.8 | 1:9.8 | Crystalline | Crystalline | Crystalline | Amorphous |
| 3.6 | 1:4.9 | Crystalline | Crystalline | Amorphous | Amorphous |
| 7.2 | 1:2.5 | Crystalline | NS | Amorphous | NS |
| 14.4 | 1:1.2 | Crystalline | NS | Amorphous | NS |

*NS = not synthesized

Table 2 shows results of experiments in which the Mg:Ca ratio was measured at synthesis and in the final material

TABLE 2

Mg:Ca and P:Ca ratio in stock solutions and after synthesis of AMCP, as determined by ICP.

| | At synthesis (reagents) Final [Mg] mM | At synthesis (reagents) Mg:Ca ratio | At synthesis (reagents) P:Ca ratio | Actual (determined in material by ICP) Mg:Ca ratio (±SD) without protein | Mg:Ca ratio (±SD) with protein | P:Ca ratio (±SD) without protein | P:Ca ratio (±SD) with protein |
|---|---|---|---|---|---|---|---|
| 1 | 14.4 | 1:1.2 | 1:0.9 | 1:1.60 (0.004) | 1:1.18 (0.01) | 1:0.84 (0.03) | 1:0.69 (0.01) |
| 2 | 7.2 | 1:2.5 | 1:0.9 | 1:5.77 (0.02) | 1:2.79 (0.05) | 1:1.26 (0.03) | 1:1.03 (0.01) |
| 3 | 3.6 | 1:4.9 | 1:0.9 | 1:10.83 (0.004) | 1:10.27 (0.2) | 1:1.35 (0.01) | 1:1.33 (0.02) |
| 4 | 1.8 | 1:9.8 | 1:0.9 | 1:17.4 (0.3) | 1:17.43 (0.1) | 1:1.40 (0.02) | 1:1.36 (0.03) |
| 5 | 0.9 | 1:19.7 | 1:0.9 | 1:32.6 (0.5) | 1:26.2 (0.3) | 1:1.41 (0.04) | 1:1.41 (0.02) |
| 6 | 0 | N/A | 1:0.9 | N/A | 1:217* (8) | 1:1.52 (0.04) | 1:1.48 (0.02) |

N/A: Not applicable

*[Mg] derived from the protein

The present inventors further found that incorporation of the cargo molecules increases phase stability of the material in aqueous environments, which is beneficial for biomedical applications. This was exemplified in tissue culture media, where amorphous magnesium-substituted calcium phosphate nanoparticles loaded with protein cargo molecule, in this case the protein bovine serum albumin, required significantly longer to convert to hydroxyapatite (HA) than the corresponding unloaded amorphous magnesium-substituted calcium phosphate (Table 3).

TABLE 3

Effect of protein incorporation on the phase stability of Mg-stabilised ACP ([Mg] = 3.6 mM) in tissue culture media made according to the general protocol described above at pH 10.0, washed with acetone twice and dried overnight in oven.

| Time (mins) | no BSA | With BSA |
|---|---|---|
| 15 | ACP | ACP |
| 30 | ACP | ACP |
| 60 | HA | ACP |
| 180 | HA | ACP |
| 320 | HA | — |
| 24 hours | — | ACP |

Samples centrifuged and washed twice with pH 10.0 water

Samples resuspended in D10 (same volume as synthesis mixture)

Samples centrifuged and washed with pH 10.0 water

Samples centrifuged and washed with acetone twice

Dried Overnight in Oven

In addition, the present inventors have found that increasing the pH of synthesis above pH 8.0 may produce amorphous magnesium-substituted calcium phosphate compositions with improved phase stability as compared to the corresponding materials synthesized at pH 8.0 as used by Boskey & Posner (1974). Accordingly, it is preferred that the pH during steps (a) and/or (b) is greater than 7.5, preferably at least pH 8.0, more preferably at least pH 8.5, and most preferably at least pH 9.0.

Formulations and Uses

The amorphous magnesium-substituted calcium phosphate compositions of the present invention may be formulated for use as agents for delivering the entrapped cargo materials, such as cargo molecules or cargo nanoparticles, and may be used to treat and/or prevent, conditions that respond to the cargo molecules, in vitro and/or in vivo. As described elsewhere, compositions for use in diagnostic applications are also disclosed. Accordingly, the compositions of the present invention may comprise, in addition to one or more of the amorphous magnesium-substituted calcium phosphate compositions of the present invention, a pharmaceutically acceptable excipient, carrier, buffer, stabiliser or other materials well known to those skilled in the art. Such materials should be non-toxic and should not significantly interfere with the efficacy of the solid phase materials for the application in question.

The precise nature of the carrier or other component may be related to the manner or route of administration of the composition. These compositions may be delivered by a range of delivery routes including, but not limited to, gastrointestinal delivery, especially orally and nasogastric delivery; parenteral delivery, including injection; or by implant at specific sites, including prosthetics that may be used for this purpose or mainly for another purpose but have this benefit. In particular, the compositions can be used in gene transfection or introduction of nucleic acid sequences, vaccination, delivery of therapeutic agents, ex-vivo manipulation of cells for re-injection to same or different, recipient and delivery of nutrients. In particular, the compositions can be used in vaccination, and in the treatment or prevention of autoimmune diseases, as part of cancer therapy, treatment of food allergies and/or intolerances, including de-sensitisation, and treatment or prevention of inflammatory bowel disease, most especially Crohn's disease.

As described herein, the present invention provides medical uses in which the amorphous magnesium-substitute calcium phosphate compositions are used to deliver a wide range of therapeutic substances, principally to cells present in the gastrointestinal tract, such as cells present in the Peyer's patches and in the mesenteric lymph nodes, in locations such as the ileum and caecal patches of the caecum, especially the appendix.

In one embodiment, the present invention may be used for the treatment or prevention of cancer, especially as vaccine compositions. For example, the compositions of the present invention may be used as vaccines for the treatment of Myeloid Leukaemias. This may include using cargo molecules which are fusion proteins of BCR-ABL (Breakpoint Cluster Region-Abelson) resulting from the formation of the Philadelphia chromosome in Myeloid Leukaemias such as Chronic Myelogenous Leukaemia (CML), Acute Lymphoblastic Leukaemia and Acute Myelogenous Leukaemia (AML), BCR-ABL fusion proteins, including portions or synthetic analogues thereof, may be incorporated within AMCP, and optionally combined with an immune-stimulatory (tolerance breaking) agent, such as MAMP, to induce robust, adaptive immune T cell responses to the aberrant cancer fusion proteins. Another cancer fusion protein target that may be used as a cargo molecule for therapeutic vaccination is GAG-ONC (Rous sarcoma virus). Details of these proteins are available as follows:

GAG-ONC:

http://www.nlm.nih.gov/cgi/mesh/2011/MB_cgi?mode=term=gag-onc+Fusion+Proteins

BCR-ABL:

http://www.nlm.nih.gov/cgi/mesh/2011/MB_cgi?mode=term=Fusion+Proteins,+bcr-abl&field=entry#TreeD12.776.602.500.500.100

In a further embodiment, the present invention may be used for the treatment or prevention autoimmune diseases by using therapeutic vaccination to induce tolerance towards autoimmune T cell and auto-antibody responses. Previous research using the Experimental Autoimmune Encephalomyelitis (EAE) murine model for multiple sclerosis that therapeutic vaccination against autoimmune neuro-antigen targets can be achieved via the oral route (Song et al., The Peyer's patch is a critical immunoregulatory site for mucosal tolerance in experimental autoimmune encephalomyelitis (EAE). J. Autoimmun. 2008 June; 30(4):230-7.)

In one embodiment, the compositions of the present invention may be used for the treatment or prevention of multiple sclerosis by therapeutic vaccination, for example by incorporating one or more autoimmune central nervous system neuro-antigenic proteins into AMCP, optionally with one or more tolerance inducing agents, such as peptidoglycan, for inducing tolerogenic T cell responses to autoimmune targets. By way of illustration neuro-antigenic proteins relating specifically to the treatment of Multiple Sclerosis include Myelin Basic Protein (MBP), Proteolipid Protein (PLP), Myelin Oligodendrocyte Glycoprotein (MOG), Myelin-associated Glycoprotein (MAG), S100β Glycoprotein (SB), Oligodendrocyte-Myelin Glycoprotein (OMGP), Myelin-Associated Oligodendrocytic Basic Protein (MOBP), αβ-crystallin (CRAB) and 2'-3'-cyclic nucleotide 3'-pPhosphodiesterase (CNP) (see Crawford et al., High prevalence of autoreactive, neuroantigen-specific CD8+ T cells in multiple sclerosis revealed by novel flow cytometric assay. Blood 2004 Jun. 1; 103 (11): 4222-31.). Accordingly, one or more of these proteins, or a biologically active fragment thereof, may be used as cargo molecules.

In a further embodiment, the present invention may be used for the treatment or prevention of inflammatory bowel diseases, such as Crohn's disease and coeliac disease. Therapeutic vaccination for the treatment or prevention of inflammatory bowel diseases such as coeliac disease may be carried out by incorporating Gliadin, a prolamin (gluten protein) found in wheat, or similar proteins found in the crops of the tribe Triticeae (such as barley and rye) into AMCP with or without tolerance inducing agents (such as peptidoglycan) to induce tolerogenic T cell responses to autoimmune targets. See Di Sabatino et al. (The Lancet—25 Apr. 2009 (Vol. 373, Issue 9673, Pages 1480-1493) and In a further embodiment, the present invention may be used for the treatment or prevention of type 1 diabetes. Therapeutic vaccination for the treatment or prevention of type 1 diabetes may be carried out by incorporating glutamic acid decarboxylase (GAD) isoforms GAD67 and GAD65 into AMCP, with or without tolerance inducing agents (such as peptidoglycan), to induce tolerogenic B cell responses to autoimmune targets. See Kaufman et al. (Autoimmunity to two forms of glutamate decarboxylase in insulin-dependent diabetes mellitus. J. Clin. Invest., 1932; 89(1); 283-292.)

In a further embodiment, the present invention may be used for the treatment or prevention of autoimmune conditions such as Systemic Lupus Erythematosus (SLE). Therapeutic vaccination for the treatment or prevention of SLE may be carried out by incorporating High Mobility Group box 1 (HMGB1) and other small nuclear ribonucleoproteins (nRNPs common targets of autoantibodies in lupus and other autoimmune diseases), into AMCP with or without tolerance inducing agents (such as peptidoglycan) to induce tolerogenic B cell responses to autoimmune, targets, See Poole et al., Early Targets of nRNP Humoral Autoimmunity in Human Systemic Lupus Erythematosus. Arthritis Rheum. 2009 March; 60(3): 848-859.

In some embodiments, the amorphous magnesium-substituted calcium phosphate compositions of the present invention may be used to deliver cargo materials to cell types or biological locations that preferentially take them up. These include the Peyer's patches and mesenteric lymph nodes, present in locations of the gastrointestinal tract such as the ileum and caecal patches of the caecum, especially the appendix.

Pharmaceutical compositions for oral administration may be in a tablet, capsule, powder, gel, liquid form, sprinkle or a suitable food-stuff. A tablet may include a solid carrier, such as gelatin, or an adjuvant. Capsules may have specialised properties such as an enteric coating. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. Where the amorphous magnesium-substituted calcium phosphate nanoparticles of the present invention needs to be maintained in a solid form, e.g. to control the delivery of a component of the material, it may be necessary to select components of the formulation accordingly, e.g. where a liquid formulation of the material is made. Where the material is administered with a food-stuff, the formulation components will be chosen to be compatible with the amorphous magnesium-substituted calcium phosphate compositions and to provide suitable physicochemical and organoleptic characteristics.

For intravenous, cutaneous or subcutaneous injection, or injection at the site of affliction, the active ingredient will be in the form of a parenteraliy acceptable aqueous solution or suspension which is pyrogen-free, except for what is within the amorphous magnesium-substituted calcium phosphate compositions, and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, anti-oxidants and/or other additives may be included, as required.

The materials and compositions used in accordance with the present, invention that are to be given to an individual are preferably administered in a "prophylactically effective amount" or a "therapeutically effective amount" (as the case may be, although prophylaxis may be considered therapy), this being sufficient to show benefit to the individual clinical state. The actual amount administered, and rate and time-course of administration, will depend on the nature and severity of what is being treated. Decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found, in Remington's Pharmaceutical Sciences, 20th Edition, 2000, Lippincott, Williams & Wilkins. A composition may be administered alone or in combination with other treatments, either simultaneously or sequentially, dependent upon the condition to be treated.

Examples of the uses of the amorphous magnesium-substituted calcium phosphate compositions of the present invention include, but are not limited to, uses for the delivery of dietary mineral supplements and fortificants; therapeutic mineral supplements (e.g. as administered by i.v. and oral routes); drugs, nutrients or cosmetic carriers/co-complexes; phosphate binding agents; other binding or sequestering applications; food additives; anti-perspirants; sun-protection agents; vaccine compositions adjuvants; immuno-modulatory agents; direct cosmetic applications including exfoliating agents; bone and dental filler/cements; implant materials including brachytherapy, and imaging and contrast agents. In one embodiment, the amorphous magnesium-substituted calcium phosphate compositions of the present invention may be used as delivery platform for supplements for nutritional or medical benefit. In one embodiment, the present invention employs nanoparticles as cargo materials, for example metal-based or metal oxo-hydroxide based nanoparticles. These may be used for imaging, for example for tracking the amorphous magnesium-substituted calcium phosphate present in a subject to whom a composition of the present invention has been administered. In all formats, but most especially for fortificants, subsequent formulation, such as addition of a protective coating (e.g. lipid), may be necessary to make the material compatible with its intended usage. For example the compositions may be encapsulated for oral administration.

Role of PD-L1 in Intestinal Health and Disease, in Particular in Chrohn's Disease Antigen presenting cells (APCs) can acquire soluble and/or particulate protein antigens which they process and present polypeptides of, on their surface, in the groove of MHC. T cells may then engage the MHC via their T cell receptors (TCR) forming an MHC-antigen-TCR complex. Precisely how the T cell responds depends upon a number of factors, an important one being co-stimulatory signals from other surface molecules.

In the gastrointestinal tract, it is known that one important region of protein antigen encounter and presentation by APCs to T cells is the lymphoid follicles, exemplified by Peyer's patches of the ileum and caecal patches of the caecum, especially the appendix. It is also known that the general response in the gastrointestinal tract is one of immuno-tolerance to prevent active immune responses to all the beneficial antigens that the gut is exposed to (e.g., friendly bacteria living in the environment and food protein). Programmed death ligand 1 (PD-L1), expressed upon antigen presenting cells (APC), is a co-stimulatory molecule that in general provides strong immuno-tolerance signals to T cells and is one candidate molecule for helping maintain tolerance in the gastrointestinal tract. In one aspect of the present invention, the present inventors have found that the cells of the Peyer's patches that stain with calcein because of the present of endogenous calcium phosphate nanomineral, are representative of antigen receiving cells of intestinal lymphoid follicles and normally express distinct and mostly high levels of PD-L1. These cells are mostly CD11b and CD11c positive, typical of a population of dendritic cells in this region of the gut, and a minority are CD68 positive, typical of mature macrophages. Taken together, these observations are consistent with (a) the uptake and presentation of antigen into the lymphoid follicle immune cells by the calcium phosphate nanoparticles and (b) PD-L1 playing an important role in these specific cells to ensure that the antigen is presented in a tolerogenic context.

Surprisingly, the inventors have now found, that in Crohn's disease, these cells are almost always negative for PD-L1 or express very low levels. This suggests that failure of PD-L1 signalling in these areas, namely intestinal lymphoid follicles, is a fundamental defect in the aetiopathogenesis of Crohn's disease that can be corrected to provide therapeutic benefit to patients. Accordingly, in one aspect, the present invention provides an agent capable of increasing expression of PD-L1 in antigen-presenting immune cells present in the gut for use in a method of treating Crohn's disease. In some embodiments, the agent may be delivered to the cells using the amorphous magnesium-substituted calcium phosphate nanoparticles described herein, thereby taking advantage of their selective uptake by these cells.

By way of explanation, Programmed Cell Death Ligand 1 ('PD-L1') has a gene that encodes a 290 amino acid protein. In the main PD-L1, also known as CD274, belongs to the B7:CD28 superfamily of co-receptor molecules and it functions as an inhibitor of T cell function by dampening cytokine production and TCR signalling when bound to its receptor PD-1.

The HUGO Gene Symbol report for PD-L1 (gene name CD274; synonyms 37H1, PDCD1L1, PDCD1LG1, PDL1 and sometimes referred to as PD-1 ligand 1) can be found at http://www.genenames.org/data/hgnc_data.phg?hqnc_id=17635, which provides links to the PD-L1 nucleic acid and amino acid sequences, as well as reference to the murine and rat homologs. The amino acid sequence of full length human PD-L1 is set out in the UniProt Knowledgebase in SEQ ID NO: 1 (identifier: Q9NZQ7-1), although two other isoforms produced by alternative splicing nave been described that differ from the canonical sequence as follows: in isoform 2 amino acids 19-132 are missing (identifier: Q9NSQ7-2), while in isoform 3 there is an amino acid exchange at position 178 (178-178: K→D) and amino acids 179-290 are missing (identifier: Q9NZQ7-3).

```
MRIFAVFIFM TYWHLLNAFT VTVPKDLYVV EYGSNMTIEC

KFPVEKQLDL AALIVYWEME DKNIIQFVHG EEDLKVQHSS

YRQRARLLKD QLSLGNAALQ ITDVKLQDAG VYRCMISYGG

ADYKPITVKV NAPYNKINQR ILVVDPVTSE HELTCQAEGY

PKAEVIWTSS DHQVLSGKTT TTNSKREEKL FNVTSTLRIN

TTTNEIFYCT FRRLDPEENH TAELVIPELP LAHPPNERTH

LVILGAILLC LGVALTFIFR LRKGRMMDVK KCGIQDTNSK

KQSDTHLEET
```

Accordingly, in one aspect, the present invention is based on the novel findings that by treating these antigen presenting cells of the intestinal lymphoid follicles, so as to up-regulate the expression of PD-L1, would be of significant therapeutic benefit in the treatment, or prevention of Crohn's disease. The amorphous magnesium-substituted calcium phosphate materials of the present invention that mimic the in vivo nanomineral, could therefore be employed to deliver agents capable of up-regulating PD-L1 expression as the entrapped cargo material, having the advantage of targeting the very intestinal lymphoid follicle cells that require treatment. Such a therapeutic would need to bypass the proposed 'peptidoglycan block' if this proves to be the underlying mechanistic reason for failure of PD-L1 expression in Crohn's disease, or indeed inflammatory bowel diseases generally.

By way of some example, agents capable of inducing PD-L1 are known in the art. PD-L1 is induced in human cells by Type 1 interferons, such as IFN gamma (Seung-Jin Lee et al 2006, Dong et al 2002). This pathway has been successfully manipulated to induce or suppress PD-L1 expression in human biliary epithelial cells with the use of microRNA-513: transfection of biliary epithelial cells with an antisense oligonucleotide to miRNA-513 induced PD-L1 expression (Gong et al 2009).

The analog of viral dsRNA, polyinosinic-polycytidylic acid (poly IC), up-regulates expression of B7-H1 via activation of the nuclear factor κB(NF-κB) in epithelial cells (Keiko Kan-o et al 2013). Similarly, viral infections such as HIV are associated with virally induced up-regulation of PD-L1 on APC (Trabattoni et al 2003, Seyerl et al 2010).

Also, mycobacterial infections induce PD-L1 expression in APC (Sakai et al 2010). This may be done by stimulation with even the mycobacterial protein product, such as protein purified derivative of tuberculin (PPD), resulting in the up-regulation of PD-L1 on APC, most notably when the PPD was present in the amorphous magnesium-substituted calcium phosphate form.

In some aspects, the present invention relates to an agent that is capable of one or more of:

(a) up-regulating the expression of PD-L1; or
(b) activating PD-L1 protein; or
(c) inhibiting repression of PD-L1; or
(d) otherwise activating PD-L1 on antigen presenting cells of the intestinal lymphoid follicles for use in a method of treating Crohn's disease, or inflammatory bowel disease in general.

In related aspects, the present invention provides a pharmaceutical composition which comprises such an agent, wherein the agent is entrapped as a cargo material within an amorphous magnesium-substituted calcium phosphate material of the present invention.

In one approach, the treatment described herein may employ gene therapy to induce PD-L1 expression in the target cell: the gene therapy as described elsewhere herein in detail. In some embodiments, this may involve a cargo material comprising nucleic acid encoding PD-L1 being incorporated in the synthetic magnesium-substituted calcium phosphate compositions of the present invention for delivery to target cells with low levels or no PD-L1 expression.

In general, gene therapy approaches according to this aspect of the present invention will employ nucleic acid encoding biologically active PD-L1 polypeptide to treat a patient who is unable to synthesize the active polypeptide or unable to synthesize it at the normal level, thereby providing the effect provided, by wild-type PD-L1 and treating Crohn's disease or suppressing new outbreaks of this condition.

Vectors such as viral vectors have been used in the prior art to introduce genes into a wide variety of different target cells. Typically the vectors are exposed to the target cells so that transfection can take place in a sufficient proportion of the cells to provide a useful therapeutic or prophylactic effect from the expression of the desired polypeptide. The transfected nucleic acid may be permanently incorporated into the genome of each of the targeted cells, providing long lasting effect, or alternatively the treatment may have to be repeated periodically.

A variety of vectors, both viral vectors and plasmid vectors, are known in the art, see (U.S. Pat. No. 5,252,479 and WO93/C7282. In particular, a number of viruses have been used as gene transfer vectors, including papovaviruses, such as SV40, vaccinia virus, herpesviruses, including HSV and EBV, and retroviruses. Many gene therapy protocols in the prior art have used disabled murine retroviruses.

As an alternative to the use of viral vectors other known methods of introducing nucleic acid into cells includes electroporation, calcium phosphate co-precipitation, mechanical techniques such as microinjection, transfer mediated by liposomes and direct DNA uptake and receptor-mediated DNA transfer. In addition, the present invention provides a further means of delivering PD-L1 nucleic acid sequences to the target cells using the amorphous magnesium-substituted calcium phosphate compositions described herein.

As mentioned, above, the aim of gene therapy using nucleic acid encoding the PD-L1 polypeptide, or an active portion thereof, is to increase the amount of the expression product of the nucleic acid in cells in which the level of the wild-type PD-L1 polypeptide is absent or present only at reduced levels.

In a second approach, the therapy may be an agent that activates promoter regions of the PD-L1 gene such that it is expressed as the protein. In some embodiments, this may involve the agent being used as a cargo material incorporated in the synthetic magnesium-substituted calcium phosphate compositions of the present invention. Activators of PD-L1 expression may be found using methods of screening described herein.

In a third approach, the treatment may involve a MAMP as these are known to induce PD-L1. Examples of MAMPs are given elsewhere herein. Peptidoglycan, and peptidoglycan fragments, may or may not be useful MAMPs for the reasons described above. In some embodiments, this may involve the MAMP being used as a cargo material incorporated in the synthetic magnesium-substituted calcium phosphate compositions of the present invention.

In a forth approach, the treatment may involve a compound or mixture of compounds, in a soluble, colloidal, nanoparticulate or microparticulate form, that induce PD-L1 expression such as poly IC and interferons or other cytokines, especially type I interferons. In some embodiments, this may involve the compounds being used as a cargo material incorporated in the synthetic magnesium-substituted calcium phosphate compositions of the present invention.

In a fifth approach, the treatment may involve a biological agent, that induces PD-L1, such as a virus or bacteria, or an attenuated form thereof, mixtures and/or homogenates of such biological agents such as PPD or nucleic acid sequences. In some embodiments, this may involve the biological agent being used as a cargo material incorporated in the synthetic magnesium-substituted calcium phosphate compositions of the present invention.

In a sixth approach, the treatment may involve a treatment to inhibit the repression of PD-L1 expression in Crohn's disease, the treatment optionally being the cargo of the synthetic magnesium substituted calcium phosphate. In some embodiments, this may involve an agent capable of inhibiting the repression of PD-L1 expression being used as a cargo material incorporated in the synthetic magnesium-substituted calcium phosphate compositions of the present invention.

It will be apparent to those skilled in the art that, these approaches may be employed, alone or in any combination. Further approaches for activating PD-L1 may involve the use of one or more chemokines or cytokines (e.g., interferons), microRNAs (e.g., miR-513), peptides, proteins or glycoproteins, antibodies, enzymes, oligonucleotides and/or siRNAs or RNAi.

Methods of Screening for PD-L1 Activators

The present invention includes methods of screening for agents capable of increasing the expression of PD-L1 for use in the treatment or prevention of Crohn's disease. As explained herein, it is known that when PD-L1 is present on antigen presenting cells, such as dendritic cells, it acts as a marker that instructs T-cells to be tolerant, to the antigen being presented by that cell. Without wishing to be bound by any particular theory, the results in this application indicate that reduced levels or no expression of PD-L1 leads to a failure to induce this tolerance, and hence causes the inflammation that is at the heart of Crohn's disease. The present inventors believe that the reduced expression of PD-L1 is a therapeutic target for the treatment or prevention of Crohn's disease either by inducing expression of PL-D1 in the antigen presenting cells that receive luminal antigen. In one embodiment, this approach may use the properties of the amorphous magnesium-substituted calcium phosphate nanoparticles in targeting such cells in the gut to deliver agents capable of restoring PD-L1 function or expression.

It will be well known to those skilled in the art that to assess whether a therapeutic agent does indeed increase co-stimulatory molecule expression, such as PD-L1 expression, in intestinal lymphoid follicles a number of approaches can be taken. One approach will involve resecting or biopsying the lymphoid aggregate after treatment and comparing PD-L1 or other expression, such as by immunostaining of sections or ELISA or gene expression analysis of regions or extracted cells of the tissue taken. Results would be compared to sham treated or placebo treated cases or to samples taken at baseline. In the case of humans, specialist dyes may be used such that the intestinal lymphoid aggregates are better identified for the purpose of biopsy with endoscopy. Clearly, such techniques can be applied to patients with Crohn's disease.

Accordingly, the present invention also includes methods for the screening of candidate compounds to find PD-L1 activators, e.g. for identifying candidate agents that are capable of activating PD-L1 expression or protein activity for subsequent use or development as agents for the treatment of inflammatory bowel diseases, and Crohn's disease in particular. Conveniently, this may be done in an assay buffer to help the components of the assay interact, and in a multiple well format to test a plurality of candidate agents. The activity of PD-L1 can then be determined in the presence and absence of the one or more candidate compounds to determine whether a given candidate has increased PD-L1 expression or PD-L1 protein levels or activity.

To understand which receptors are expressed that might be engaged in the target cells by a delivered, cargo that up-regulates PD-L1, techniques may be employed to search for the receptor expression, including immunostaining and measures of gene expression. Thereafter suitable cargo that will engage the receptor and lead to PD-L1 expression can be attained through further screening studies.

By way of example, the suitable cargo molecules for use in this aspect of the present invention may be a known activator of PD-L1 or a newly identified one. Combinatorial library technology provides one efficient way of testing a potentially vast number of different substances for ability to modulate activity of a target protein such as PD-L1. Such libraries and their use are known in the art. Following identification of a candidate agent for further investigation, the agent in question may be tested to determine whether it is not lethal to normal cells or otherwise is suited to therapeutic use. Following these studies, and others that confirm its choice for in vivo therapy, the agent may be manufactured and/or used in the preparation of a medicament, pharmaceutical composition or dosage form.

In some embodiments, method of screening for PD-L1 activators may employ a cell-based assay comprising the steps of contacting cells which are capable of expressing PD-L1 with one or more candidate agents and determining whether PD-L1 expression of protein activity increases in response to a candidate agent. The method may further comprise identifying candidate agent that increase PD-L1 expression or protein activity. The present application identifies suitable cell types and phenotypes for use in such methods of screening. It is well known in the art that from the epithelial layer and elsewhere in the gut signals are derived that endow local antigen presenting cells (APCs) with a phenotype of tolerance induction when they themselves signal (Iliev, 2009, 2009; Rimoldi, 2005; Maheshwari, 2011). In vitro conditions are known that can mimic this process. It is therefore possible to take blood cells and to use a cocktail of chemicals, or indeed media from epithelial cell cultures (so called epithelial cell conditioned medium), and induce this tolerance promoting phenotype of APCs (Mann et al., 2012; den Hartog et al., 2013; Zeuthen et al., 2008; Steinbrink, 1997). It is equally possible to break this tolerance promoting process of APCs. For example, with the addition of TNF alpha. And this may mimic the process in Crohn's disease (Bamias, 2013).

In one approach, candidate agents capable of up-regulating PD-L1 may be identified from the prior art. These agents can be contacted with conditioned APCs, both alone and as cargo materials within the magnesium-substituted calcium, phosphate compositions of the present invention. The conditioned cells will be in the presence or absence of TNFalpha and/or other tolerance breaking agents. PD-L1 regulation will be assessed, for example by quantitative RT-PCR, for gene up-regulation and by antibody staining with flow cytometry for the protein. Preferably, the candidate agents identified as being capable of enhancing PD-L1 expression will be able to do so in spite of the use of agents such as TNFα to break the tolerance promoting process of the APCs.

In a second approach, a similar method may be carried out, but with APCs conditioned with medium from normal or Crohn's disease epithelial cell culture, these epithelial cells being derived from endoscopic biopsies or at surgery. Preferably, the candidate agents identified as being capable of enhancing PD-L1 expression will be able to do so in spite of the use of media conditioned by Crohn's disease epithelial cells.

In a third approach, numerous animal models exist for Crohn's disease. For example, one has been described by Adolph et al. 2013. Different models will be screened by staining of Peyer's patch sections for calcein and PD-L1. Models with similar low PD-L1 expression in calcein positive Peyer's patch APCs, to that observed in Crohn's disease, will be used to test the candidate agents for suitability as therapeutics. These could be applied in or out of the synthetic magnesium substituted calcium phosphate compositions of the present invention and applied orally, with or without enteric coating, or in perfusion or tied loop experiments or in similar surgical experiments where the potential therapeutic is in contact with the Peyer's patches for 1 or more hours. The Peyer's patches can then be excised at some time after the application of the potential, therapeutic and through staining for protein and/or in situ hybridisation for gene up-regulation, the change in PD-L1 expression assessed. Optionally, areas of the patch or even dissected single cells could be assessed by flow cytometric and/or gene, analysis techniques as described above.

In a fourth approach, in patients with Crohn's disease, potential therapeutics, optionally incorporated or not within the synthetic magnesium-substituted nanomineral, could be applied orally or rectally, with appropriate enteric coating as required to allow release in the ileum and/or large intestine. The treatment could be applied for 1 day, preferably 3 days and most preferably a week or more and the intestinal lymphoid aggregates could be biopsied before and after treatment and the change in PD-L1 expression assessed as above.

It will be clear to those in the art that all or some of the above may be used to identify the optimal therapeutic that will induce PD-L1 appropriately in APCs of the intestinal lymphoid follicles of patients with Crohn's disease.

EXPERIMENTAL

Part I: Discovery of the Endogenous Assembly of AMCP Nanoparticles and the Role in Peyer's Patches Endogenous Nanomineral of the Intestinal Lumen Distal small intestinal contents, recovered from ileostomy patients, were air dried on plastic-coated stubs for scanning electron microscopy (SEM). Extensive numbers of submicron sized particles were identified and their calcium phosphate-rich elemental composition confirmed by X-ray microanalysis (XRMA). High magnification SEM indicated that the particles were generally agglomerates of smaller, nanoparticulate structures.

To better mimic in situ dispersion, whole cross-sections of non-aqueous resin embedded murine distal small bowel were then, studied and transmission EM (TEM) used to provide greater resolution. A high density of relatively electron dense nanoparticles was visible and these were again calcium and phosphorus rich by analysis. High power TEM imaging showed that these particles were porous and selected area electron diffraction confirmed that they were not crystalline, in contrast to biological apatite or octacalcium pentophosphate which are more typically associated with biological systems.

Peyer's Patch M-Cells Transport the Endogenous Nanomineral

To determine whether these endogenously formed nanominerals of the gut lumen were transported by M-cells of the Peyer's patch epithelium, TEM analysis of murine-derived thin-sections was carried out. Non-aqueous resin was used to preserve the in situ particle structure whilst M-cells were identified by their well described stunted, or lack of, surface microvilli in contrast to neighbouring enterocytes. With this strategy, numerous disperse nanomineral structures within the M-cells were identified with size, shape, amorphous structure and X-ray elemental composition identical to those characterised in the gut lumen. On rare occasions, one or two such particles at the M cell-enterocyte interface were observed, but found no evidence of these particulates within the regular enterocytes: instead they appeared restricted to, and in abundance, within cells with typical M-cell features.

Endogenous Mineral in Antigen Presenting Cells of the Peyer's Patch

M-cells appear to have little capacity for antigen processing but, rather, pass on luminal molecules to underlying immune cells. Although the endogenous nanomineral was identified by TEM to be within M-cells in a disperse fashion, nanoparticulate clusters can be observed by light microscopy when accrued in vesicular (i.e. lysosomal) compartments of APCs. Thus, frozen sections of both human and murine Peyer's patches were studied, and modified Von Kossa staining for mineralised phosphate revealed large numbers of positive cells within the deeper sub-epithelial dome. Fluorescent, calcein staining, for mineralised calcium, confirmed these observations. A detector for back scattered electrons fitted to the SEM allowed the identification of electron dense regions in the same sub-epithelial dome area that were, again, calcium and phosphorus rich by X-ray microanalysis. Both human and murine tissue samples were similarly positive for these features.

Common antibody-based fluorescent markers were used to confirm an APC phenotype of these mineral-positive cells in murine and human Peyer's patches. As artefactual cell antigen staining can occur with these cells, presumably through adsorption of the stain to the intracellular mineral, care was taken to ensure that, for phenotyping, all stains showed cellular distributions typical of the anticipated antigen location and not simply co-incidental with the cellular areas rich in mineral. In addition to the nuclear stain, double staining, namely calcein for the mineral plus one phenotypic marker, was used at a time. The majority of human and murine calcein$^+$ cells were strongly positive for CD11b, CD11c and HLA-DR with a distinct sub-population that were CD68$^{hi}$). The (peripheral) monocyte marker, CD14, was absent while this and the positive antigens noted above were all confirmed in specific positive-control tissues that contained cells expressing these markers (see Methods). Thus, overall, the phenotype of the mineral-positive cells of the Peyer's patch sub-epithelial dome was consistent, with mononuclear APC residing in that zone.

Individual intracellular vesicles, containing the calcein$^+$ mineral could be discerned within the sub-epithelial dome APCs. In this region, TEM imaging of non-aqueous resin embedded thin sections demonstrated individual nanomineral morphology identical to luminal and epithelial M-cell particles. Similarities by imaging were confirmed analytically for Ca, Mg and P content, using standard less elemental quantification of X-ray microanalysis spectra from similar thin sections of Per's patches and luminal contents.

In Situ Scanning TEM (STEM) Characterisation and 3D Nanotomography

Clusters of the nanoparticulate mineralised calcium were often observed in the sub epithelial dome APCs, perhaps explained by adhesion to internal vesicle membranes which is well known for nanominerals in cell lysosomes. A region from such a cluster was imaged using high angle annular dark field (HAADF) STEM to enable sufficient contrast with unstained non-aqueous-resin-embedded specimens. A HAADF-STEM tilt series was recorded and used to reconstruct a 3-D model.

The Endogenous Nanomineral Traps and Transports Luminal Bacterial Fragments and Dietary Antigen The homogenous formation of abundant, porous luminal calcium phosphate nanomineral and its marked transport across M-cells into Peyer's patch APCs, lead us to question function. Calcium phosphates excel at trapping organic molecules and, under certain circumstances, enter cells with their bound material. Here, therefore, a constitutive "cargo ship" function of the endogenous nanomineral was considered whereby soluble, luminal organic macromolecules could be trapped and then transported to gut APCs. To test whether orally delivered dietary protein antigen might cross the Peyer's patch epithelium associated with the endogenously formed nanomineral, BALB/c mice were fed with Texas Red®-labelled ovalbumin. The protein detected in Peyer's patches was almost solely compartmentalised with nanomineral-positive cells of the sub-epithelial dome. Since it remained possible that ovalbumin and the fluorochrome were cleaved during digestion, only the latter being associated with the nanomineral, the Peyer's patch sections for ovalbumin were also directly stained. Using the Huygens maximum least expected deconvolution algorithm, to maximise resolution with confocal microscopy, clear co-localisation was again observed. Additionally, there were close but separated intracellular calcein and protein signals, as would be expected if the nanomineral dissolves intra-lysosomally, first unmasking, and then releasing its cargo.

MAMPs, such as peptidoglycan, are present ubiquitously in the lumen of the distal gastrointestinal tract, including the ileum, due to the turnover of commensal bacterial flora. Peptidoglycan has been identified in human and murine apical aspects of the gut mucosa by antibody 2E9, which recognises only degraded/free peptidoglycan and not that present in whole bacteria. Experiments using 2E9 antibody experiments showed that, similar to dietary derived ovalbumin, peptidoglycan was compartmentalised with the nanomineral of the APCs, again in terms of inseparable fluorescent signals and also as separate but closely adjacent signals. We confirmed that, just as for the Peyer's patch, AMCP nanomineral was also observed in caecal patch sub-epithelial immune cells. Collectively these data indicate that the endogenous intestinal AMCP nanomineral forms in the lumen and enters APCs of intestinal immune-inductive sites, namely the caecal and Peyer's patches, predominantly via epithelial M cells', see FIG. 11A. The intestinal immune response to orally-delivered protein involves cooperation between Peyer's patches and mesenteric lymph nodes. In particular, migration of APCs to the mesenteric lymph nodes implies functional activity (i.e. antigen presentation) and we confirmed that mesenteric lymph nodes in mice had significant numbers of AMCP nanomineral+ cells (FIG. 11B).

DISCUSSION

Although enumeration of endogenous nanomineral particles in the human gastrointestinal lumen exceeds current analytical capability, these observations on human and murine small intestinal contents suggest that these occur in enormous numbers. For example, if median [Ca] and [P] are 4.2 mM and 10 mM respectively, in 1 L/24 h of succus entericus (intestinal juice) of the human ileum, and a third precipitates at mean 6:10 molar ratio (P:(Ca+Mg) since Mg substitutes for Ca) to form, on average, 100 nm diameter spherical amorphous particles (with P packing density similar to that, in octacalcium phosphate) with a 50% void volume (porosity) then it is estimated that ~$2.10^{14}$ particles will be present. It is likely that this nanomineral has not been previously observed/characterised because the particles are small and processing techniques for analysis must be carefully controlled to avoid aqueous degradation.

There are several notable and unusual features to this nanomineral. First, it remains as discrete (disperse), self-assembled nanoparticles. Whilst, the formation of endogenous nanominerals is well known (e.g. ferrihydrite in the ferritin molecule core, or biological apatite as the primary crystallite structure of bone) these are templated by organic substrates. In contrast, ectopic self-assembled mineralisation normally involves uncontrolled precipitation and aggregation of the particles. Secondly, the minimum ion activity product required to form amorphous calcium phosphate, in preference to more crystalline calcium phosphates, is generally too high in vivo, and so biological amorphous calcium phosphate is rare. In humans evidence for the occurrence of amorphous calcium phosphate in bone, for example, is poor, although it may play a transient role in initiation of matrix vesicle biomineralisation. Even then, amorphous calcium phosphate, being the least stable of the calcium phosphate phases, rapidly converts to octacalcium phosphate and onwards to apatitic-type structures. In the gut, however, the calcium, phosphate nanomineral appears stable in amorphous form from the lumen right through to delivery to the mucosal immune cells and is presumably stabilised by the relatively high Mg content and substantial organic cargo. Importantly, as the most readily soluble form of calcium, phosphate, lysosomal conditions would allow rapid dissolution of the endogenous nanomineral and release of the organic cargo derived from the gut lumen. Indeed, a third unique property of these endogenously formed nanominerals is their extensive porosity and their notable functional capacity to trap luminal molecules and deliver them to Peyer's patch APCs via the M-cell portal.

These experiments identified peptidoglycan and dietary protein antigen as two targets for trapping and immune cell-delivery by the amorphous calcium phosphate nanoparticles, and other molecules could similarly be employed as cargo molecules, and, for example be chaperoned to Peyer's patch APCs. The gastrointestinal immune system has an apparent array of mechanisms to sample luminal material and generate appropriate (tolerogenic as the default) immune responses. This work shows that amorphous calcium phosphate nanoparticles that trap cargo molecules such as luminal antigens and microbial-associated molecular patterns (MAMPs), with delivery across M-cells to sub-epithelial APCs, may form an important part of the gut's immune surveillance and tolerance network. Indeed, the brush border enzyme network may destroy free or particle-adsorbed MAMPs and antigens so that only nanomineral-incorporated organic molecules can safely traverse the Peyer's patch apical mucosa to underlying immune cells.

Overall, these aspects of the present invention provide new insights into the interplay between nutrition, gut physiology and the mucosal, immune, system mediated by self-assembled endogenous nanoparticles. In particular they suggest answers for (a) why the Peyer's patch has such a remarkable ability for the uptake of non-biological nanoparticles in the ~20-250 nm range (b) how, under constitutive conditions, luminal antigen and MAMPs can reach APCs of the deeper, sub-epithelial dome without prior enzymatic degradation or engaging epithelial responses (c) why there are 'obligatory' endogenous calcium losses into the gut lumen.

Part II: The Development of Synthetic Mimetics of ACP Nanoparticles, Their Characterisation and Use as Carriers of Cargo Based on the above findings in Part I that in the gastrointestinal tract, calcium ions and phosphate ions precipitate and form nanoparticles that trap organic molecules present in the lumen for delivery to gut mucosal immune cells, the present inventors carried out experiments to produce synthetic mimetics of endogenous intestinal calcium phosphate nanoparticles and to determine whether they were stable and capable of acting as carriers of cargo molecules.

Example 1

Synthesis of Amorphous Calcium Phosphate (AMCP)

Synthetic Amorphous Calcium Phosphate ("ACP") particles were prepared using a modified protocol of Boskey and Posner (Boskey and Posner, 1974). The modification consisted of the addition of magnesium ($Mg^{2+}$) and/or by carrying out the synthesis in the presence of a range of molecules capable of becoming trapped inside the AMCP particles to enhance phase stability. The synthesis process for loaded and unloaded AMCP particles was based on the rapid addition of a phosphate ($PO_4$) solution to a calcium solution both buffered at alkaline pH (typically pH 8 or 9 and Tris buffered). Initially, an amorphous calcium phosphate (ACP) phase is formed that tends to convert to more crystalline phases. The conversion process can be prevented, or at least inhibited, by the addition of $Mg^{2+}$ ions and/or by carrying out the synthesis in the presence of a wide range of molecules capable of becoming trapped inside the AMCP particles.

By way of illustration, 18.1 g Trizma-base $C_4H_{11}NO_3$ was dissolved in 1 L ultra-pure water to make a 0.15M solution of TRIS buffer. The pH was adjusted to pH 8 by drop-wise addition of hydrochloric acid (TRIS-HCl). Solution A was prepared, by adding 2.6 g $CaCl_2.2H_2O$ to 500 mls TRIS-HCl buffer containing 0.73 g of $MgCl_2.2H_2O$ and the pH adjusted to pH 8. Solution B was prepared by adding 2.6 g $(NH_4)$ $2HPO_4$ to 500 mls TRIS-HCl buffer and the pH adjusted to pH 8. Equal amounts of solution A and R were then mixed together (v/v) and rotated for an hour at room temperature. After an hour, the resulting particles were washed twice in pH 10 water and once in acetone. Particles were then dried overnight at 50° C. and weighed. On average 2.19 mg±0.14 (n=4) of dried AMCP powder was recovered per ml of particle preparation.

Example 2

Synthesis of Amorphous Calcium Phosphate (AMCP) Particles Containing a Protein ACP particles were prepared as described in Example 1 with the modification that protein as exemplified by bovine serum albumin (BSA) or avidin was added to solution A to yield 1 mg/ml. Equal amounts of solution A and B were then mixed together (v/v) and rotated for an hour at room temperature. After an hour, the resulting particles were washed twice in pH 10 water and the resulting pellet of particles dissolved in citric acid buffer (10 mM, pH 3). The level of protein incorporated into the particles was measured by the Bradford protein assay. On occasions, particles were also dried overnight at 50° C. and powders weighed (n=4, after two washes in acetone). On average 242.9 μg±47.77 (n=8) BSA or 157.76 μg avidin (n=1) was present in 2.39 mg±0.14 ACP powder (n=4).

Example 3

Synthesis of Amorphous Calcium Phosphate (AMCP) Particles Containing a Protein and a Crude Bacterial Motif AMCP particles were prepared as described in Example 1 with the modification that BSA and dyed (Remazol Blue Brilliant; Zhou et al, 1988) crude peptidoglycan from *S. Aureus* were added to solution A to yield 1 mg/ml and 100 μg/ml, respectively. Equal amounts of solution A and B were then mixed together (v/v) and rotated for an hour at room temperature. After an hour, the resulting particles were washed twice in pH 10 water. The resulting pellet of particles was dissolved in citric acid buffer for quantification purposes and the level of protein incorporated into the particles was measured by the Bradford protein assay while the amount of dyed peptidoglycan was read, at 595 nm. On average 270.5 μg±13.95 (n=3) BSA and 45.20±0.99 μg (n=4) crude Pg were present in 1.98 mg ACP powder (n=1).

Example 4

Synthesis of Amorphous Calcium Phosphate (AMCP) Particles Containing a Protein and a Soluble Bacterial Motif AMCP particles were prepared as described in example 1 with the modification that BSA and soluble peptidoglycan from *E. Coli* were added to solution A to yield 1 mg/ml and 100 μg/ml, respectively. Equal amounts of solution A and B were then mixed together (v/v) and rotated for an hour at room temperature. After an hour, the resulting particles were washed twice in pH 10. The resulting pellet of particles was dissolved in citric acid buffer for quantification purposes and the level of protein incorporated into the particles was measured by the Bradford protein assay while the amount of soluble peptidoglycan was assessed by the adapted Periodic Schiff Assay (Jugdaohsingh R, 1999). On average 232.9 μg±14.62 (n=5) BSA and 29.47±12.83 μg (n=9) soluble Pg were present in AMCP particles.

Example 5

Synthesis of Amorphous Calcium Phosphate (AMCP) Particles Containing a Protein and a Soluble Complex Polysaccharide AMCP particles were prepared as described in Example 1 with the modification that BSA and soluble starch were added to solution A to yield 1 mg/ml and 100 μg/ml, respectively. Equal amounts of solution A and B were then mixed together (v/v) and rotated for an hour at room temperature. After an hour, the resulting particles were washed twice in pH 10. The resulting pellet of particles was dissolved in citric acid buffer for quantification purposes and the amount of soluble starch incorporated into the particles was assessed by the adapted Periodic Schiff Assay (Jugdaohsingh R, 1999) and found to be 45.99 μg (n=1).

Example 6

Synthesis of Amorphous Calcium Phosphate (AMCP) Particles Containing a Protein and an Immunogen AMCP particles were prepared as described in Example 1 with the modification that BSA was added to solution A to yield 1 mg/ml while Protein Purified Derivatives (PPD from *M. Tuberculosis*) was added to solution 3 to yield 200 μg/ml. Equal amounts of solution A and B were then mixed together (v/v) and rotated for an hour at room temperature. After an hour, the resulting particles were washed, twice in pH 10. The resulting pellet of particles was dissolved in citric acid buffer for quantification purposes. Levels of proteins incorporated into the particles were measured, by the Bradford protein assay and by the PAS assay. On average 188.3 μg±24.54 (n=4) BSA and 51.61±20.07 μg (n=3) PPD were present in ACP particles.

Example 7

Synthesis of Amorphous Calcium Phosphate (AMCP) Particles Containing Protein and a Cytokine AMCP particles were prepared as described in Example 1 with the modification that BSA was added to solution A to yield 1 mg/ml while Thymic Stromic Lymphopoietin (TSLP) was added to solution B to yield 100 or 1 ng/ml. Equal amounts of solution A and B were then mixed together (v/v) and rotated for an hour at room temperature. After an hour, the resulting particles were washed twice in pH 10 water. The resulting pellet of particles was dissolved in citric acid buffer for quantification purposes and the level of TSLP incorporated into the particles was measured by an ELISA specific for TSLP and found to be 1.38 ng (n=1) and 25.73 pg (n=1), respectively.

Example 8

Synthesis of Amorphous Calcium Phosphate (AMCP) Particles Containing Iron Oxide-Containing Particles and Protein or "AMCP/BSA/Fe"

AMCP particles were prepared as described in Example 2 with the modification that the solution of $Ca^{2+}/Mg^{2+}$/BSA was additionally mixed with 100 μg/ml iron oxide solution. The resulting solution was then mixed with an equal volume of $PO_4$ solution to allow particle precipitation.

Structural Characterisation of Synthetic Calcium Phosphate Particles

Synthetic calcium phosphate particles prepared in the absence (i.e. AMCP/BSA) or presence of small iron oxide nanoparticles (i.e. AMCP/BSA/Fe) were fixed in the non-aqueous resin 'Quetol 651' and sections cut to 70 nm thicknesses. Tomography experiments based on high-angle annular dark-field (HAADF) imaging in the scanning transmission electron microscopy (STEM) mode were performed at 200 kV on a FEI Tecnai F20 electron microscope tilting the sample from −42° to +70° at 2° intervals about a single, axis using a Fischione 2020 ultra-high-tilt tomography holder. Tilt series were aligned and reconstructed using Inspect3D software and AM IRA software was used for visualization.

Quantification of the Organic Fraction Contained Within the Calcium Phosphate Particles Following synthesis, particles containing cargo molecules such as BSA or sPg (alone or in conjunction) were centrifuged at 1,500 rpm (5 mins) and supernatants collected. Next, particles were washed twice in pH 10 water. Then, for quantification purposes, particles were dissolved in 100 mM citric acid buffer (pH 3) to release the organic material. Total protein content was measured using the Bradford protein assay (as per manufacturer's protocol, Bio-Rad Laboratories, UK) while Pg matter was quantified using a modified Periodic Acid Schiff assay (PAS; Jugdaohsingh R et al, 1999). This assay relies on the formation of a purple complex whose absorbance is proportional to the amount of polysaccharides in solution. Samples and standards (100 μl) were first incubated with 92 mM sodium, periodate in 0.5 M sulphuric acid (10 μl/well, 37° C. for 30 min with occasional shaking) and then with 2.7% sodium arsenite in 0.68 M HCl (20 μl/well) at room temperature on a plate shaker (40 mins). Following the addition of Schiff's reagent (50 μl/well; Merck KGaA, Germany) and a further 30 mins incubation at 37° C., the plate was read at 540 nm. Concentration, of polysaccharides were determined against a standard curve soluble Pg (0-250 μg/ml) and prepared in the lysate of AMCP/BSA particles to account for sample matrix.

Size Measurement

Nanoparticle Tracking Analysis was performed on a Nanosight NS500 (Nanosigbt, Amesbury, UK) using NTA2.2 Analytical Software. For each experiment samples were measured in technical triplicates (90 sec each) and results averaged. Data are shown as mean of three independent experiments.

Determination of Elemental Composition

Synthetic calcium phosphate particles were dissolved in 5% HNO3 (Sigma-Aldrich Company Ltd., Dorset, UK) prior to ICP-OES analysis. Samples were analysed using the JY2000 ICP-OES (Horiba Jobin Yvon Ltd., Stanmore, UK) and Ca and P were detected at 396.847 nm and 177.440 nm, respectively. Quantification was performed using external standards (Calibration Standard Solutions 1000 ppm, Fisher Scientific UK Ltd, Leicestershire, UK; 0.5-50 ppm). Total Ca and P were obtained from particle suspensions collected after synthesis or after dilution in TCM while aliquots of particle suspensions were ultra-filtered (MWCO 3 kDa, 10 min, 12.000 rpm) to determine the soluble Ca and P fractions. Background correction was performed using the Ca and P values obtained from D10 (i.e. the TCM) that had been subjected to the same treatment as particle suspensions. The elemental particulate fraction was then calculated as the difference between total and soluble elemental composition.

Cell Isolation

Leukocyte cones (n=7) were purchased from the National Blood Service, Cambridge, UK, and peripheral blood mononuclear cells (PBMC) isolated by density centrifugation with Lymphoprep (Axis Shield Diagnostics Ltd, Dundee, Scotland) as separating medium. Briefly, blood was diluted with HBSS (Sigma-Aldrich) and 25 ml of diluted blood carefully layered over 10 ml Lymphoprep. After 20 rain centrifugation (800×g, brake off) the resulting layer of mononuclear cells was collected, three times washed in HBSS, and then re-suspended in R10 (RPMI-1640 medium (Sigma-Aldrich), supplemented with 10% heat inactivated fetal calf serum (PAA Laboratories Ltd., Dorset, UK), 100 U/ml penicillin, 100 ug/ml streptomycin, and 2 mM 1-glutamine (all Sigma-Aldrich)) at a concentration of 5.106 cells/ml for further enrichment of monocytes.

To this end, a second density centrifugation was performed as described by Martinez. In brief, the density medium. Percoll (Sigma-Aldrich) was osmolarised to 285 mOsm by mixing 9.25 parts of Percoll with 0.75 parts of 10×DPBS (with calcium and magnesium; Sigma-Aldrich), and was then diluted to 46% (v/v) in R10. The PBMC suspension was carefully layered, over an equal volume of 46% solution of 285 mOsm Percoll. After 30 min centrifugation (400×g, brake off) the resulting layer of PBMC enriched in monocytes was collected, three times washed in HBSS and finally re-suspended, at 1.106 cells/ml in R10. Monocyte-enriched PBMC routinely showed a viability of ≥95% as determined by trypan blue (Sigma-Aldrich) exclusion assay (and consisted to 57.29% of CD14+ monocytes as measured by flow cytometry?).

Cell Stimulation

Culture and stimulation of monocyte-enriched PBMC were performed in sterile 15 ml Falcon tubes (Starlab UK Ltd, Milton Keynes, UK) at $1.10^6$ cells/ml and at 37° C./5% CO2. Freshly isolated monocyte-enriched PBMC were rested overnight following which they were replenished with fresh tissue culture medium (namely D10; DMEM (Sigma-Aldrich) supplemented with 10% heat-inactivated, serum, 100 U/ml penicillin, 100 μg/ml streptomycin, and 2 mM L-glutamine). $5.10^6$ cells were then stimulated for 3 hrs with vehicle D10 as negative control or with 4.4 μg/ml soluble peptidoglycan (from *Escherichia coli*; Source Bioscience plc, Nottingham, UK) either in soluble (sPg) or particulate (AMCP/BSA/sPg) form. This was achieved, by preparing 40 μg/ml sPg in D10, or synthesising AMCP/BSA/sPg particles with 50 μg/ml sPg (to account for sPg losses during particle washes), and adding 125 μl stimulant per ml of cell suspension. After 3 hrs stimulants were removed and cells washed twice in HBSS before they were lysed with Nucleic Acid Purification Solution (Life Technologies Ltd., Paisley, UK.) and cell lysates stored at −80° C. prior to RNA isolation.

RNA Extraction

Total RNA was purified using an Abi Prism 6100 Nucleic Acid PrepStation (Applied Biosystems, UK) following manufacturer's instructions and including a wash step with AbsoluteRNA wash solution (Applied Biosystems), again as per manufacturer's instructions. Concentration and purity of eluted RNA were determined on a NanoDrop ND-1000 Spectrophotometer (Labtech International Ltd, UK). On occasions and to increase nucleotide concentration, a second purification procedure was performed using RNeasy MinElute™ Cleanup Kit. (Qiagen Ltd, Manchester, UK) according to manufacturer's instructions. Samples were stored, at −80° C. until further microarray processing.

Microarray Processing

Total RNA (100 ng) was labelled using an Ambion WT expression kit (Life Technologies, Bleiswijk, The Netherlands) and hybridized to human whole genome Genechip Human Gene 1.1 ST arrays coding 19.732 genes, (Affymetrix, Santa Clara, Calif.). Sample labelling, hybridization to chips and image scanning was performed according to manufacturer's instructions.

Microarray Data Analysis

Microarray analysis was performed using MADMAX pipeline for statistical analysis of microarray data. For further analysis a custom annotation was used based on reorganized oligonucleotide probes, which combine ail individual probes for a gene. Only genes that had at least five probes present on the array were taken into account. Expression values were calculated using robust, multichip average (RMA) method, which includes quantile normalisation. Microarray data were filtered, and probe sets with expression values higher than 20 on more than four arrays were considered to be expressed and selected for further statistical analysis. In addition, an Inter Quartile Range (IQR) cut-off of 0.25 was used to filter out genes that showed little variation between the conditions. Significant differences in expression were assessed using paired Intensity-Based Moderated T-statistic (IBMT [5]). Genes were defined as significantly changed when the p value was <0.01.

To assess similarity of gene regulation by peptidoglycan in soluble and particulate form only genes that were significantly changed by at least one of the two treatments were considered. For those, the average signal log ratios (SLR; logarithmic fold change) of each stimulant compared to control treatment were calculated and visualised in a correlation plot [where each dot represents a single gene]. [The line of perfect, correlation was overlaid on the data and borders corresponding to twofold up- and down-regulation calculated by adding +1 or −1 to each point of the line of perfect correlation.]

Results

Synthetic Mimetics Generate Porous Amorphous Calcium Phosphate Nanoparticles

Figure 1:
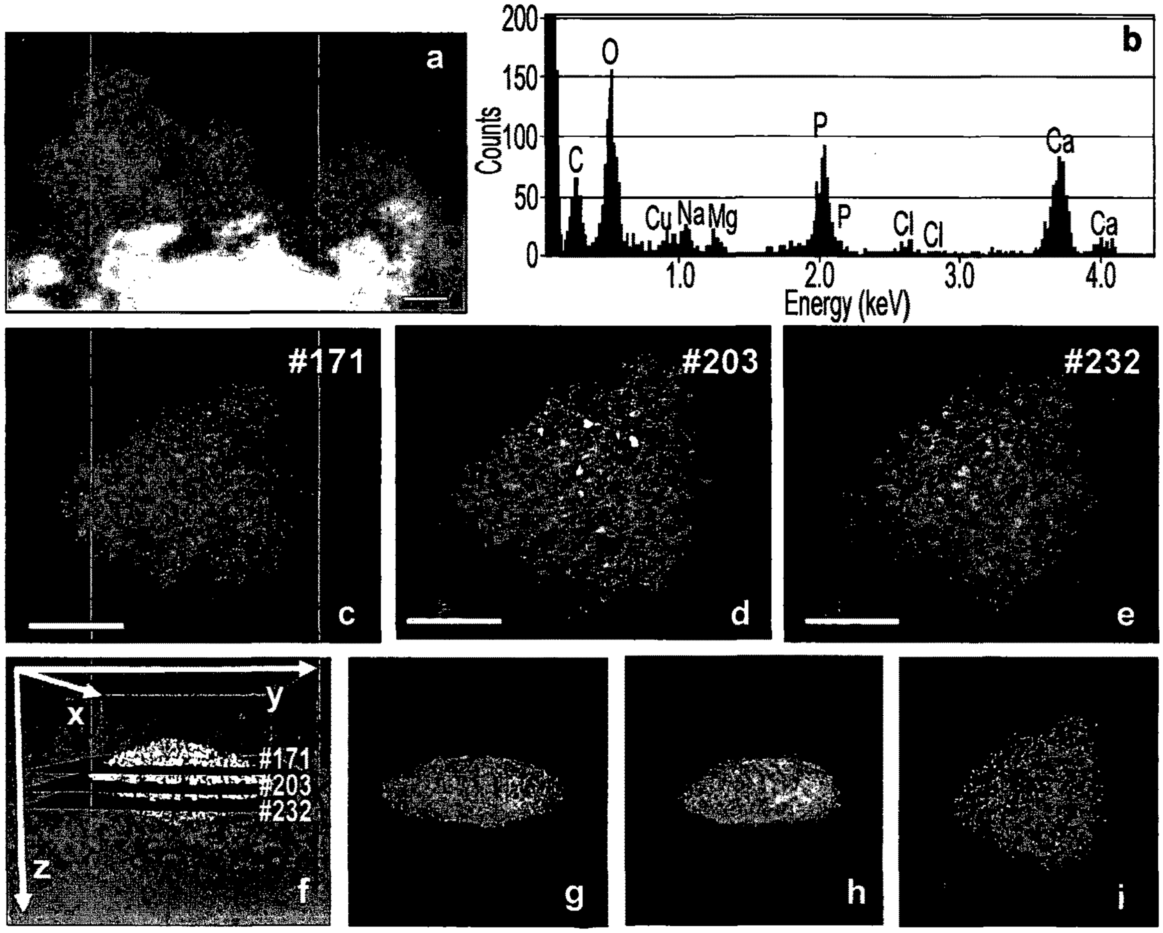
FIG. 1. STEM characterisation of synthetic AMCP nanoparticles: a—High angle annular dark-field STEM image of synthetic AMCP particle clusters (Scale bar 20 nm) and b—example elemental composition by energy dispersive X-ray microanalysis, c-e—A series of orthoslices of a synthetic AMCP particle (Scale bar 20 nm) revealing a detailed inner structure (f-i) from the reconstructed volume (f) by means of several orthoslices through the XY plan and (g-i) transparency views through the YZ, XZ and XY orientations, respectively.

Calcium phosphate that were synthesised using a modified protocol from Boskey produced, homogenous nanoparticles in the same size range to their in vivo intestinal counterparts (FIG. 1A) and comprised predominantly calcium, phosphorus and magnesium (FIG. 1B). Consistent with our prior in vivo findings, analysis by high angle annular dark field scanning transmission electron microscopy (HAADF-STEM; FIG. 1C-E), and then 3D-reconstruction of protein-loaded synthetic AMCP clusters (FIG. 1F-I) confirmed the porous nature of the particles (pore average size of 1-3 nm).

Synthetic Mimetics Template Around Inorganic and Organic Components

Figure 2:
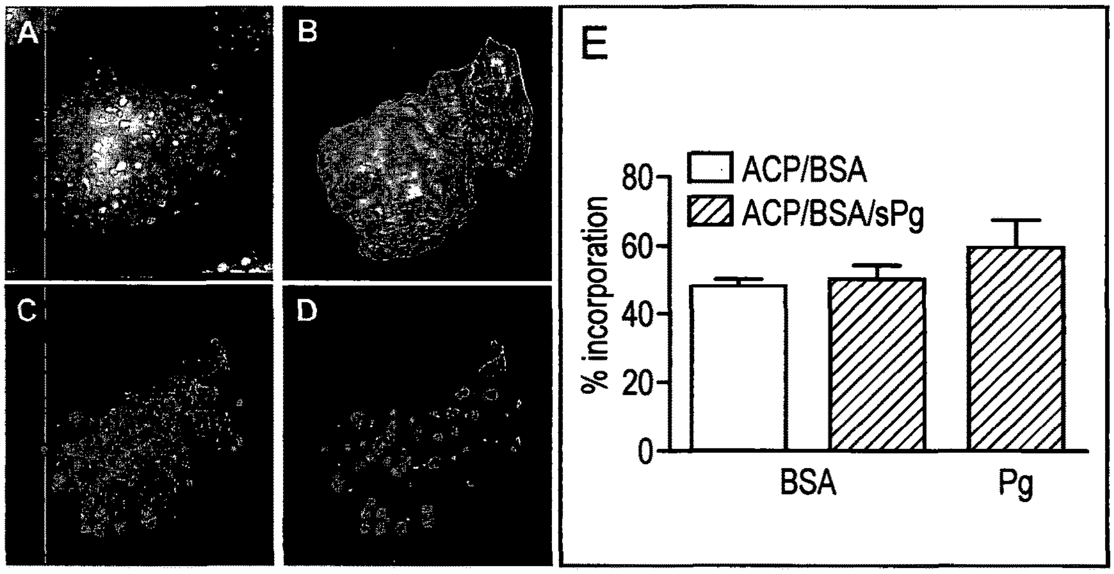
FIG. 2. A. Transmission electron microscopy and B. 3D tomography reconstruction of AMCP particles formed in the presence of iron oxide nanoparticles (see Example 3) and snowing how some are trapped within the AMCP as shown in C-D. E % incorporation of BSA and Pg in AMCP particles as prepared in examples 2 and 3.

The results showed that porosity was in part owed to the particles templating around inorganic and organic components that were present in the mother solutions (e.g. iron oxide nanoparticles, proteins and/or bacterial components). Indeed, when synthetic mimetics were prepared in the presence of iron oxides nanoparticles, TEM showed synthetic amorphous calcium phosphate nanoparticles with small nano-iron particles incorporated throughout (FIG. 2A). Scanning transmission electron microscope (STEM) tomographic reconstruction of a synthetic amorphous calcium phosphate nano-iron particle additionally confirmed the uniform internal and external distribution of the smaller nano-iron particles (FIG. 2B-D). Overall, synthetic mimetics were found to incorporate 50-70% of added organic, material (FIG. 2E).

In further experiments, cargo molecules including Muramyl dipeptide (MDP), Lipopolysaccharides (LPS), Poly I:C and Retinoid acid (RA) have been shown to be incorporated in synthetic AMCP nanoparticles according to the present invention.

Synthetic Mimetics Remain Stable Under Cell Culture Conditions

Figure 3:
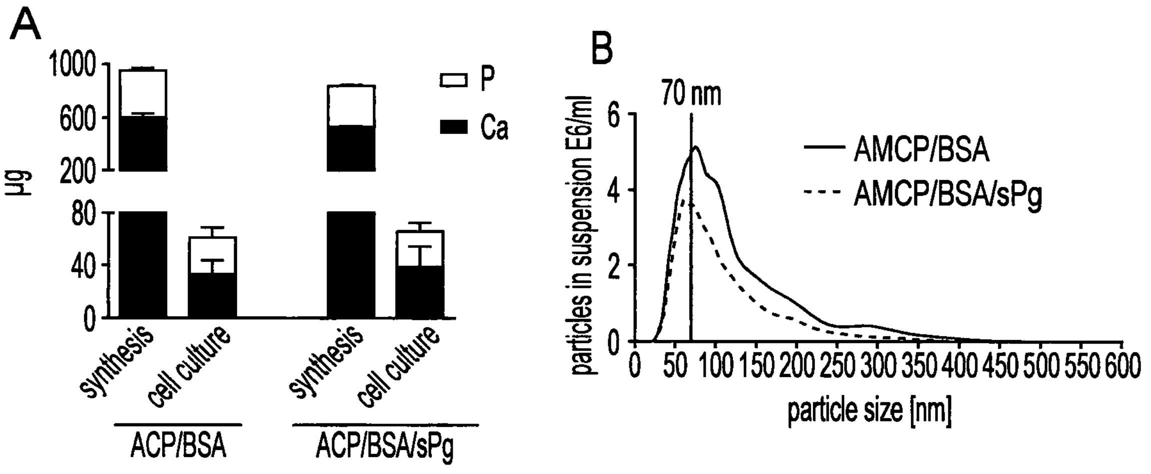
FIG. 3. A. ICP-OES analysis of Ca and P elements present in AMCP particles following synthesis and after dilution in tissue culture medium, B Size distribution of AMCP particles prepared as in Examples 2 and 4 (after re-suspension and dilution in tissue culture medium) and analysed by nanotacking analysis (NTA) using the nanosight.

Having successfully generated mimetics for intestinal endogenous nanomineral, and to further understand their relevance/function in vivo, we first verified whether amorphous calcium phosphate nanoparticles kept their structural and chemical properties when tested in cell culture conditions. As shown in FIG. 3, mimetic calcium phosphate in the presence of their cargo kept their Ca to P ratio and their average size of 70 nm.

Synthetic Mimetics are a Silent Antigen Delivery Platform

Figure 4:
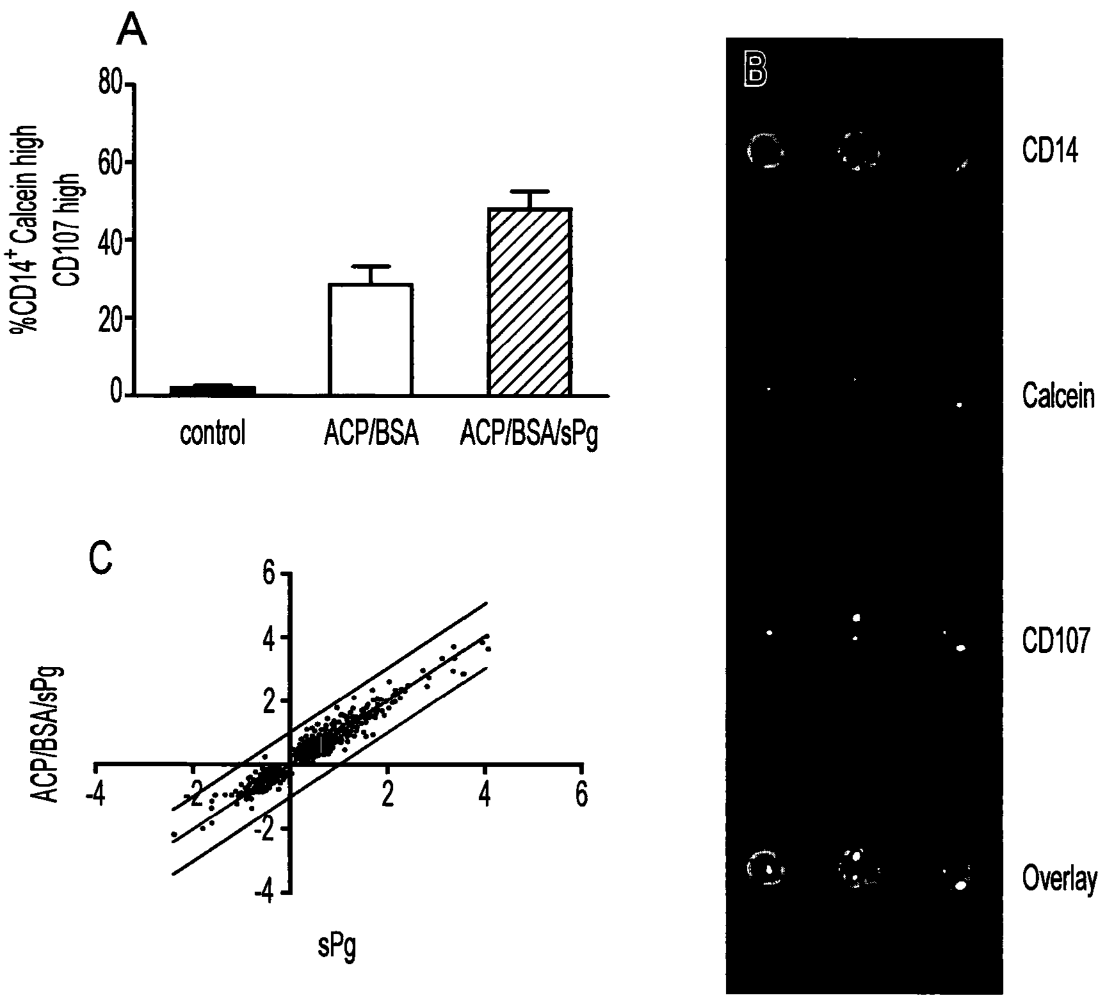
FIG. 4. A. Mean percentage of dual Calcein high CD107a high CD14+ APC within PBMC after 3 h incubation with AMCP/BSA and AMCP/BSA/Pg as measured by flow cytometric imaging (n=4). B. Representative images of CD14+ cells showing internalized particles (Calcein+) and particle co-localisation with the lysosomal marker CD107a measured by flow cytometric imaging (data from PBMC of 1 healthy control is shown). C. Signal log ratios (SLR) for AMCP/BSA/sPg vs. control were plotted on the y-axis, SLR for sPg vs. control were plotted on the x-axis. Each dot represents a single gene. The curve of perfect correlation was overlayed on the data and borders corresponding to linear 2-fold up-/down-regulation (traditionally the minimum fold change required to indicate a potential 'difference') calculated by adding +1 or −1 to each point of the line of perfect correlation.

Investigations were then carried out to investigate whether these particles were well taken up by primary immune cells and whether their uptake would modulate the immune responses to the cargo carried therein. Incubation with synthetic mimetics proved safe as no cell death ensued. Secondly and as shown in FIG. 4, these nanoparticles (FIG. 4B, calcein) were efficiently taken up by monocytes (FIG. 4B, CD14) and transported to lysosomal compartments (FIG. 4B, CD107 and overlay). Furthermore, it was interesting to notice that while uptake of particles containing bacterial components (i.e. Pg) seemed greater (FIG. 4A), the particles per se did not change the gene expression profile obtained when the same dose of peptidoglycan was delivered on its own (FIG. 4C). FIG. 10 shows the average log 2 expression values of genes, after 3 hour exposure to synthetic AMCP, correlated against, those of vehicle control treatment (n=7). This demonstrates that cells challenged with protein-loaded synthetic AMCP nanoparticles displayed a similar transcriptomic 'signature' to that of unchallenged (control) cells. Theoretical line of perfect correlation is shown in black while the borders corresponding to two-fold up- and down-regulation are shown in red. In summary, synthetic mimetics of the endogenous intestinal calcium phosphate nanominerals proved, to be a safe and suitable platform for antigen delivery, and unlike other calcium phosphates, deliver their cargo in a silent/inert fashion.

Part III: Cellular Properties of Amorphous Calcium Phosphate Nanoparticles

Figure 5:
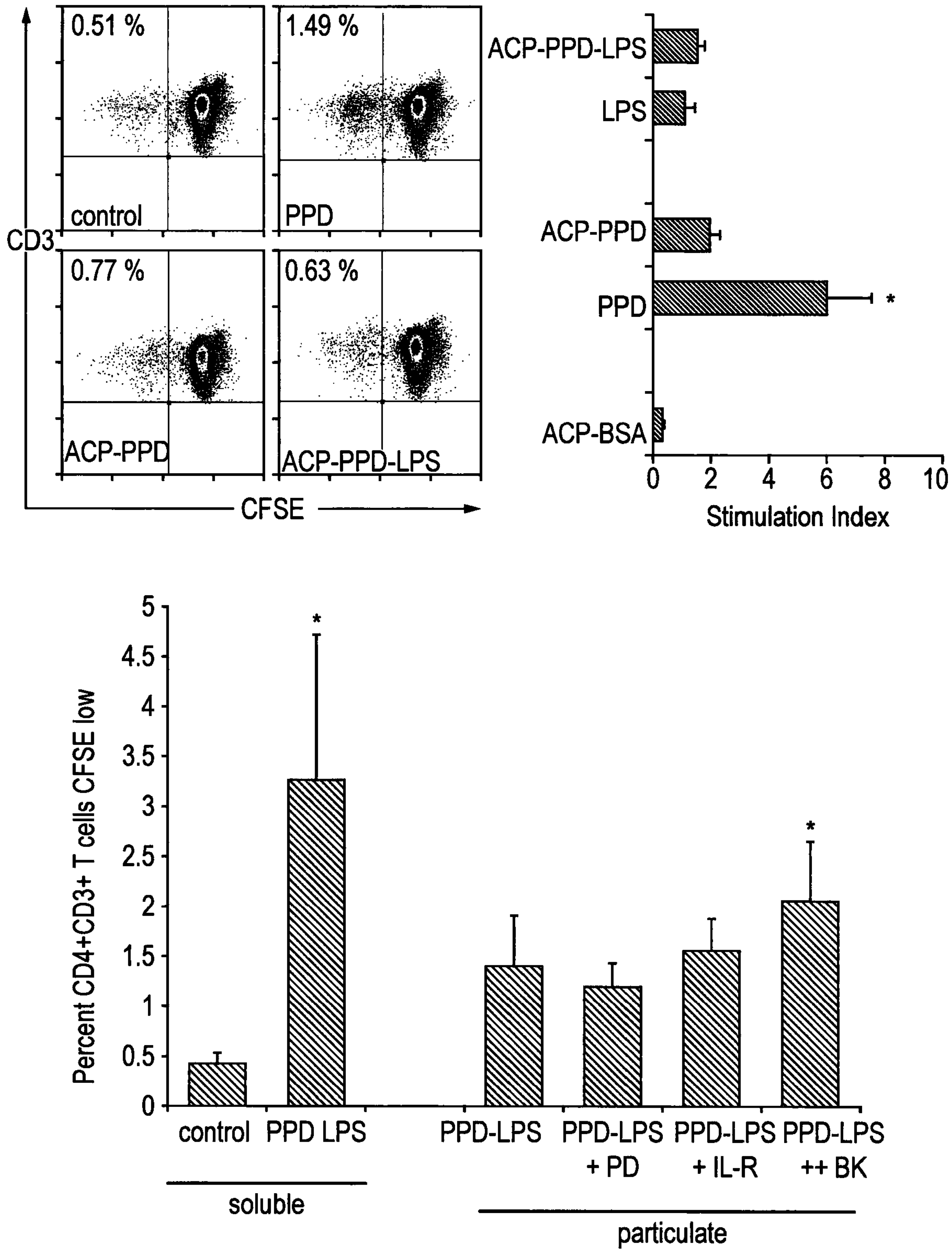
FIG. 5: Dual Carriage of Lipopolysaccharide (LPS) and T cell antigen PPD inhibits PPD antigen specific CD4+ T cell proliferation. Top left: Example flow plots showing CD4+ CD3+ dividing cells (CFSE low) in a CFSE proliferation assay; cells within a live lymphocyte gate were gated for CD4 and plotted CD3 versus CFSE. Top Right: Proliferation of CD4+CD3+ T cells in PBMC at day 5 in response to soluble and particulate PPD antigen/antigen-LPS combination Average data from 5 PPD responders is shown. CD4+ CD3+ CFSE low cells within the PBMC population in response to stimulation displayed as stimulation indices. Bottom: Further CFSE CD4+CD3+ T cell proliferation T cell assays with PD-L1 and IL-10R blocking. Average data from 6 PPD responders is shown. All Proliferation assays a PPD response was considered significant if the proliferating fraction was 2% or more and had a stimulation index of 4 or above.

Reduced Antigen Specific CD4 T-Cell Responses to Antigen-Lipopolysaccharide Co-Delivered by Intestinal Amorphous Calcium Phosphates Nanoparticle Mimetics This data demonstrates the inhibition of antigen specific T responses by particulate carriage of MAMP is not restricted to that of peptidoglycan and additionally includes lipopolysaccharides co-delivered with T cell antigen by the amorphous magnesium-substituted calcium phosphate materials of the present invention (FIG. 5).

AMCP and the Inflammasome

Figure 6:
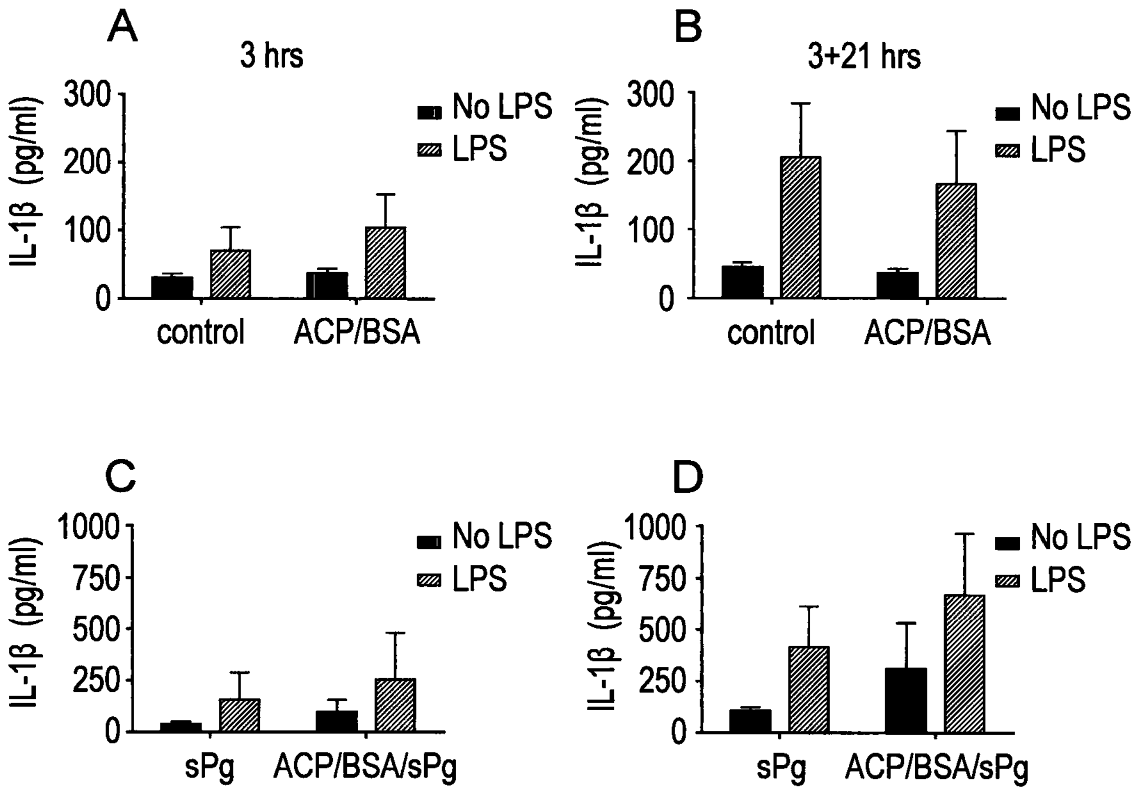
FIG. 6. IL-1β secretion from PBMC that were first pre-stimulated with LPS for 3 hours (10 ng/ml, striped columns), or without (solid columns), to induce pro-IL1β and then further incubated (3 hours) with a negative control (i.e. tissue culture medium), AMCP/BSA (A-B), sPg and AMCP/BSA/s Pg (C-D).

PBMC from 2-4 subjects were first pre-stimulated with LPS for 3 hours (10 ng/ml, striped columns), or without (solid columns), to 5 induce pro-IL1β and then further incubated (3 hours) with a negative control (i.e. tissue culture medium) or with ACP/BSA. As shown in FIGS. 6A and B, ACP/BSA did not induce IL-1β responses any different to that observed for the negative control at any of the time points studied. This was also true for particles carrying an additional peptidoglycan (sPg) component into their cargo (FIG. 6C-D).

While ACP/BSA particles did not seem to significantly modulate the responses to Pg at the IL-1β level (FIG. 7A), these however seemed to increase the secretion of the anti-inflammatory IL-10 (FIG. 7B).

Overall, the data demonstrate that synthetic mimetics of the endogenous calcium phosphate nanomineral do not activate the inflammasome platform, are able to deliver their cargo to the cells, do not modulate IL-1β responses to Pg but may rather increase anti-inflammatory signals. This means that the amorphous magnesium-substituted calcium phosphate (AMCP) nanoparticles of the present invention have the property of not masking or altering the antigen presentation of the cargo molecules to cells which have taken up the nanoparticles. This means that the AMCP nanoparticles may be used as a delivery agent for the cargo molecules that substantially does not result in an adjuvant effect caused by the AMCP nanoparticles themselves.

Part IV: The Role of PD-L1 Expression in Crohn's Disease Methods

Snap frozen human ileal tissue sections containing Peyer's patch were purchased from a tissue bank (Tissue Solutions, UK) with appropriate ethics in place. Control samples were from the resection margins of patients with tumours or ulcerative colitis (3 with Ileal carcinoid tumours, 2 with adenocarcinoma of the colon, 1 with malignant melanoma of the small intestine and 2 with ulcerative colitis). The Crohn's disease samples were from patients with different Crohn's disease anatomical locations (3 ileal, 1 ileocaecai, 2 with both ileal and large bowel involvement and 1 colonic only). Section staining and confocal imaging were undertaken in pairs (or multiples thereof) such that one Crohn's section was always accompanied by one non-Crohn's section with identical treatments to both. Hence, all samples were equally sectioned and co-stained.

Peyer's patches were cryo-sectioned (Leica CM3G5Q5) at 14 μm and collected on SuperFrost® slides (Thermo Scientific, USA) and allowed to air dry for 30 min at room temperature.

After fixation in 4% formaldehyde (4° C., 15 min), human sections were washed with Tris buffered saline (pH 8.0) and incubated with mouse anti-Human PD-L1 [(M1H1) eBioscience (14-15983)] primary antibody for four hours at 4° C. After further washing in Tris buffered saline (pH 8.0), the slides were then incubated with Alexa Fluor® 568 Goat Anti-Mouse [IgG (H+L), Invitrogen Life Technologies (A11004)] secondary antibody for two hours at 4° C. To allow detection of nano-mineralised calcium phosphate, sections were then washed in three changes of Tris buffered saline (pH 8.0), for 5 min each and incubated with calcein Tris-HCL solution for 1.5 hr, at 4° C. in the dark. Following incubation, the sections were washed carefully with three changes of Tris buffered saline (pH 8.0), for 5 min each and finally counterstained with the nuclear dye To-Pro-3 (Invitrogen Life Technologies, 1 μm). After three changes of Tris buffered saline (pH 8.0), for 1 min, sections were permanently mounted with ProLong® gold antifade reagent (Invitrogen, UK).

Sections were imaged with a Leica DMIRE2 microscope (Leica Microsystems, Germany) at 488, 568 or 633 nm, fitted with diode Ar/ArKr and HeNe lasers, using a ×63, 1.2 NA water objective lens. Data were recorded using the Leica Confocal Software (v2.61) and images processed, using the open-source ImageJ software, identical imaging and data collection routines were applied to Crohn's disease and Non-Crohn's disease sections.

RESULTS AND CONCLUSIONS

Consistently, the imaging showed similar numbers of Calcein positive cells in the sub-epithelial dome of Peyer's patch lymphoid follicles from both Crohn's and non-Crohn's tissue samples. However, whilst the Calcein positive cells also showed high expression of PD-L1 in the tissue samples from non-Crohn's disease subjects, and again consistently so, they were mostly PD-L1 negative, or, at the most, PD-L1 low in the Crohn's disease samples. Presence or absence of tumours or inflammation in the samples imaged could not explain these observations. Similarly, site of disease (i.e., whether ileal, colonic or both; could not explain these findings. There was no relationship to age either. The conclusion of this work is that failure to appropriately express PD-L1 on cells that receive and present luminal antigen in the intestinal lymphoid follicles underlies the cause of Crohn's disease because this antigen will not be presented in a tolerogenic context. Whilst not wishing to be bound by any particular theory, the present, inventors believe that an inherent failure in these cells to up-regulate PD-L1 in response to peptidoglycan, that is similarly delivered by the luminal nanomineral, explains why these cells are so universally low in PD-L1 in Crohn's disease.

REFERENCES

The following references are expressly incorporated by reference for all purposes in their entirety.

Boskey & Posner, J. Phys. Chem., 77(19): 2313-2317, 1973.
Boskey & Posner, Mat, Res. Bull. 9: 907-916, 1974.
Zhao et al., Chemistry Central Journal, 5: 40-47, 2011.
Li & Weng (J. Mater. Sci.: Mater. Med., 18: 2303-2308, 2007.
Jugdaohsingh et al. P.N.A.S., 99(6): 3394-3399, 1999.
Iliev et al., Mucosal. Immunol., 2(4): 340-350, 2009.
Iliev et al., Gut, 58(11): 1481-1489, 2009.
Rimoldi et al., Nat Immunol, 2005. 6(5): 507-514, 2005.
Maheshwari et al., Gastroenterology, 140(1): 242-253, 2011.
Mann et al., Inflamm. Bowel Dis., 18(7): 1275-1286, 2012.
den Hartog et al., Int. Arch. Allergy Immunol., 162(3): 225-36, 2013.
Zeuthen et al., Immunology, 123(2): 197-208, 2008.
Steinbrink et al., J. Immunol., 159(10): 4772-80, 1997.
Bamias et al., PLoS One, 8(8): p. e72594, 2013.
Adolph et al., Mature, 2013.
Sakai et al., Int. Immunol., 22(12): 915-25, 2010.
Lee et al., FEBS Lett., 580(3): 755-762, 2006.
Dong et al. Nat Med., 8(8): 793-300, 2002.
Kan-o et al., Bioohem Biophys Res Commun., 435(2): 195-201, 2013.
Seyerl et al., Eur J Immunol., 40(2): 321-329, 2010.
Trabattoni et al., Blood, 101(7): 2514-20, 2003.
Gong et al., J Immunol., 132(3): 1325-33, 2009.

The invention claimed is:

1. A method of treating a condition by delivering a biologically active cargo material to the gastrointestinal tract, the method comprising administering to a subject in need of treatment a composition comprising amorphous magnesium-substituted calcium phosphate (AMCP) which entraps the biologically active cargo material that is capable of promoting PD-L1 expression, thereby enabling the cargo material to be delivered to a site of interest in the gastrointestinal tract, wherein said condition is selected from Crohn's disease, or inflammatory bowel disease, wherein the cargo materials are selected from the group consisting of muramyl dipeptide (MDP), lipopolysaccharides (LPS), polyinosinic:polycytidylic acid (Poly I:C) and retinoic acid (RA).

2. The method of treatment of claim 1, wherein the magnesium-substituted calcium phosphate is amorphous as determined by X-ray diffraction.

3. The method of treatment of claim 1, wherein the X-ray diffraction pattern of the amorphous magnesium-substituted calcium phosphate lacks one or more peaks associated with the X-ray diffraction pattern of crystalline hydroxyapatite.

4. The method of treatment of claim 1, wherein the amorphous magnesium-substituted calcium phosphate is capable of dispersing to form nanoparticles that are capable of uptake by cells in the gastrointestinal tract.

5. The method of treatment of claim 4, wherein the nanoparticles are capable of uptake by gut mucosal immune cells.

6. The method of treatment of claim 1, wherein the composition delivers the biologically active cargo material to Peyer's patches or to Mesenteric Lymph Nodes (MLN).

7. The method of treatment of claim 1, wherein the amorphous magnesium-substituted calcium phosphate comprises aggregated nanoparticles that are capable of dispersing to deliver the biologically active cargo molecule to the site of interest.

8. The method of treatment of claim 7, wherein the nanoparticles are metal-based nanoparticles or metal oxo-hydroxide based nanoparticles.

9. The method of treatment of claim 1, wherein the amorphous magnesium-substituted calcium phosphate is a silent delivery platform that does not cause an adjuvant response to the amorphous magnesium-substituted calcium phosphate at the site of interest that differs substantially to the response to the biologically active cargo material alone.

10. The method of treatment of claim 1, wherein the ratio of Mg:Ca in the amorphous magnesium-substituted calcium phosphate is selected from at least 1:25, at least 1:20, at least 1:10, at least 1:5, at least 1:4 and 1:3.

11. A method of treating a condition by delivering a biologically active cargo material to the gastrointestinal tract, the method comprising administering to a subject in need of treatment a composition comprising amorphous magnesium-substituted calcium phosphate (AMCP) which entraps the biologically active cargo material that is capable of promoting PD-L1 expression, thereby enabling the cargo material to be delivered to a site of interest in the gastrointestinal tract, wherein said condition is selected from Crohn's disease, or inflammatory bowel disease, wherein said cargo material is polyinosinic:polycytidylic acid (Poly I:C).

12. The method of claim 1, wherein said cargo material further comprises protein antigens, bioactive cytokines, peptidoglycans, low molecular weight organic molecules, a nutrient, a nanoparticle, a therapeutic molecule, DNA or RNA and nanoparticles.

* * * * *

SEQUENCE LISTING

```
<160> NUMBER OF SEQ ID NOS: 1

<210> SEQ ID NO 1
<211> LENGTH: 290
<212> TYPE: PRT
<213> ORGANISM: Homo sapiens

<400> SEQUENCE: 1

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Pro Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205
```

-continued

```
Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290
```